United States Patent
Koffas et al.

(12)

(10) Patent No.: US 6,537,786 B2
(45) Date of Patent: Mar. 25, 2003

(54) GENES ENCODING EXOPOLYSACCHARIDE PRODUCTION

(75) Inventors: Mattheos Koffas, Wilmington, DE (US); James M. Odom, Kennett Square, PA (US); Siqun Wang, Wilmington, DE (US); Tao Wang, Hockessin, DE (US); Rick W. Ye, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/934,899

(22) Filed: Aug. 22, 2001

(65) Prior Publication Data

US 2002/0102697 A1 Aug. 1, 2002

Related U.S. Application Data

(60) Provisional application No. 60/229,944, filed on Sep. 1, 2000.

(51) Int. Cl.$^7$ ................................................. C12P 19/04
(52) U.S. Cl. .......................... 435/101; 435/41; 435/72; 435/183; 435/193; 435/252.3; 435/320.1; 536/23.2
(58) Field of Search ........................... 435/41, 72, 101, 435/183, 193, 252.3, 320.1; 536/23.2

(56) References Cited

FOREIGN PATENT DOCUMENTS

| WO | WO 87/05938 A1 | 10/1987 |
|---|---|---|
| WO | WO 99/54475 A2 | 10/1999 |

OTHER PUBLICATIONS

Wei et al., Biochem. Biophys. Res. Commun, 226 (3), 607–612, 1996.
Huang, J. and Schell, M., Mol. Microbiol. 16(5), 977–989, 1995.
Pique, N. et al., Unpublished Genbank No. AAC44433.
Becker, A et al., Mol. Microbiol. 16(2), 191–203, 1995.
Nakano, Y. Biochem. Biophys. Acata 1442: 409–414, 1998.
Sanford et al., Pure & Appl. Chem. 56: pp. 879–892, 1984.
Sutherland, Trends Biotechnol, 16(1): pp. 41–46, 1998.
Ielpi et al., J. Bacteriol. 175: 2490–2500, 1993.
Katzen et al., J. Bacteriol., 180: pp. 1607–1617, 1998.
Chou et al., Biochem. Biophys. Res. Commun. , 233(1), pp. 265–269, 1997.
Stingele et al., J. Bacteriol. 178: pp. 1680–1690, 1996.
Blattner et al., Science 277: pp. 1453–1474, 1997.
Bourgoin et al., Plasmid 40: pp. 44–49, 1998.
Bourgoin, F., et al., Gene 233: pp. 151–161, 1999.
Drummelsmith, J. Et. Al., Molecular Microbiology, vol. 31(5):1321–1332, 1999, Gene Products Required for Surface Expression of the Capsular Form of the Group 1 K Antigen in *Escherichia coli* (09a:K30).
Drummelsmith, J. Et. Al., Database Swissprot, Accession No.: Q9X4B7, XP002195766, Nov. 1, 1999, Putative Outer Membrane Lipoprotein WZA.
Heilig, R., Database Swissprot, Accession No.: Q9UZH4, XP002195767, May 1, 2000, Polysaccharide Biosynthesis Related Protein.
Sankhe S K Et. Al., Abstr. Pap. Am. Chem. Soc.; 195 Meet., MBTD45 Coden: ACSRAL, 1988, XP008002452.

*Primary Examiner*—Nashaat T. Nashed
*Assistant Examiner*—Christian L. Fronda

(57) ABSTRACT

Genes have been isolated from a Methylomonas sp encoding elements of the exopolysaccharide biosynthetic pathway. The genes and gene products are the first isolated from an organisms capable of utilizing single carbon (C1) substrates as energy sources. The genes are useful for engineering other C1 utilizing microorganisms to make altered levels of exopolysaccharide which is used in a variety of commercial applications.

3 Claims, 1 Drawing Sheet

Figure 1:
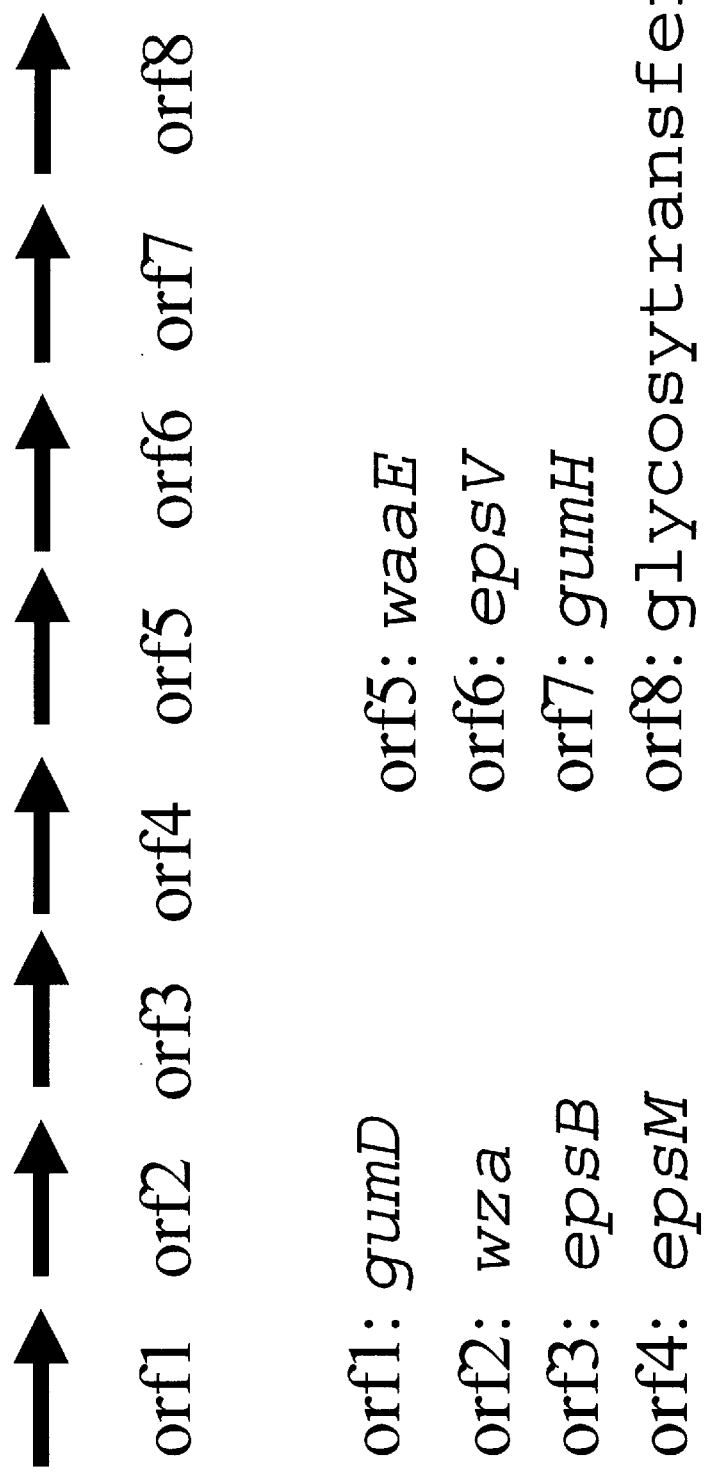

Gene Cluster for Exopolysaccharide Biosynthesis orf1  orf2  orf3  orf4  orf5  orf6  orf7  orf8 orf1: *gumD*
orf2: *wza*
orf3: *epsB*
orf4: *epsM*
orf5: *waaE*
orf6: *epsV*
orf7: *gumH*
orf8: glycosytransferase

SEQUENCE LISTING

<160> NUMBER OF SEQ ID NOS: 18

<210> SEQ ID NO 1
<211> LENGTH: 873
<212> TYPE: DNA
<213> ORGANISM: Methylomonas 16a

<400> SEQUENCE: 1

```
atgaaagtta ccaaagccgt ttttcccgtt gccggactgg gcacccggtc attgcccgca        60
accaaggccg ttgccaagga aatgttgccg gtggtggaca agccgctgat tcagtatgcg       120
gtggaagagg ccgtggccgc cggcatcgac acgatgattt tcgtgatcgg tagaaacaag       180
gaatccattg ccaaccattt cgataaatcc tacgaactga aaaaggaact ggaaaaaagc       240
ggcaagaccg atttgctgaa aatgctgcgg gagattttgc ccgcgcatgt gtcctgcgta       300
ttcgtgcgtc aagcggaggc tctgggtttg ggcatgcgg tgcattgcgc caagccggtg       360
gtcggcaacg agccgtttgc ggtgatcttg ccggatgact tgatcgagga cggcgagcgc       420
ggttgcatga agcagatggt ggatttgttc gacaaagagc aaagcagcgt attggggta       480 gagcgggtcg atcccaagga aacccataag tacggcatcg tcgaacatgc cgaaacctcg       540
cccagagtcg gttggttgag ttccatcgtc gagaaaccca aacccgaagt ggcgccctcc       600
aatatcgcgg tggtcgggcg ctacatcttg acgccggcca tttttcaaaa aatcgagaac       660
acggggcgcg gcgccggcgg cgaaattcaa ttgaccgatg cgattgccgc gttgatgaaa       720
gacgaacgcg ttttgtccta tgaattcgaa ggcaatcgct acgactgcgg ttccaagttt       780
ggttttttgt tggccaatgt cgaatatggc ttgctgcaca aggaaatcaa agccgaattc       840
gccaactatc tgaaacaacg cgtcagcaaa atc                                     873
```

```
<210> SEQ ID NO 2
<211> LENGTH: 293
<212> TYPE: PRT
<213> ORGANISM: Methylomonas 16a

<400> SEQUENCE: 2

Met Thr Met Lys Val Thr Lys Ala Val Phe Pro Val Ala Gly Leu Gly
  1               5                  10                  15

Thr Arg Ser Leu Pro Ala Thr Lys Ala Val Ala Lys Glu Met Leu Pro
             20                  25                  30

Val Val Asp Lys Pro Leu Ile Gln Tyr Ala Val Glu Glu Ala Val Ala
         35                  40                  45

Ala Gly Ile Asp Thr Met Ile Phe Val Ile Gly Arg Asn Lys Glu Ser
 50                  55                  60

Ile Ala Asn His Phe Asp Lys Ser Tyr Glu Leu Glu Lys Glu Leu Glu
 65                  70                  75                  80

Lys Ser Gly Lys Thr Asp Leu Leu Lys Met Leu Arg Glu Ile Leu Pro
                 85                  90                  95

Ala His Val Ser Cys Val Phe Val Arg Gln Ala Glu Ala Leu Gly Leu
            100                 105                 110

Gly His Ala Val His Cys Ala Lys Pro Val Val Gly Asn Glu Pro Phe
        115                 120                 125

Ala Val Ile Leu Pro Asp Asp Leu Ile Glu Asp Gly Glu Arg Gly Cys
130                 135                 140

Met Lys Gln Met Val Asp Leu Phe Asp Lys Glu Gln Ser Ser Val Leu
145                 150                 155                 160

Gly Val Glu Arg Val Asp Pro Lys Glu Thr His Lys Tyr Gly Ile Val
                165                 170                 175

Glu His Ala Glu Thr Ser Pro Arg Val Gly Trp Leu Ser Ser Ile Val
            180                 185                 190

Glu Lys Pro Lys Pro Glu Val Ala Pro Ser Asn Ile Ala Val Val Gly
        195                 200                 205

Arg Tyr Ile Leu Thr Pro Ala Ile Phe Gln Lys Ile Glu Asn Thr Gly
    210                 215                 220

Arg Gly Ala Gly Gly Glu Ile Gln Leu Thr Asp Ala Ile Ala Ala Leu
225                 230                 235                 240

Met Lys Asp Glu Arg Val Leu Ser Tyr Glu Phe Glu Gly Asn Arg Tyr
                245                 250                 255

Asp Cys Gly Ser Lys Phe Gly Phe Leu Leu Ala Asn Val Glu Tyr Gly
            260                 265                 270

Leu Leu His Lys Glu Ile Lys Ala Glu Phe Ala Asn Tyr Leu Lys Gln
        275                 280                 285

Arg Val Ser Lys Ile
    290

<210> SEQ ID NO 3
<211> LENGTH: 1419
<212> TYPE: DNA
<213> ORGANISM: Methylomonas 16a

<400> SEQUENCE: 3
atgccactcg gtttgggaaa tatcttcaac gggctgttca agcaatacgg gcacacggtg     60
atcctgttgt tgagggttat cgacgtggtc atgttattgg gcgcggcctg gctggcgcat    120 tattttggt tgcatgacag cgtcatcgat cagcattacc gtttcgtgat tgccctgggt    180
```

-continued

```
atcttgggtg cgatcatatt tttcgagatc ggccaggtgt atcggccgtg gcgcaatgac    240
gcgatgcgcg gcgaaattcc ccgcatcatc agagcctggt tgctggcctt gctgacggtg    300
gtgtccatcg tggccctggt cagattgcat ttttggtttg gttccagtta tcgctggatc    360
gcctcctggg gcggtttggg gctgttcttc gtactggcgg cccgcggtgt gctggcacag    420
gtgttgaagt ggttgcgtgc acggggctgg agccagggggc gcatcattct ggtgggtttg    480
aatcagatgg ccgtcgccgt cagtcggcaa ttgaatcact cttcctgggc cggtttgcag    540
gtgattggtt atgtcgatga ccgggccgaa gaccggctgg cggtggcgga ttattcgctg    600
ccacgcctgg gcaagttgag cgatctgcct cgtctggttt ccagacaagc cgtggatgaa    660
gtctgggtgg cgtttcctgg cgcttcgctg gccgagcggg tacagcacga attgcgccat    720
ttgccggtca gcattcgcct ggtgatcgat tgctttgcct taaacaaag caaattcctc    780 agtctgaaca cggtggccgg tatcccgacg ctggacgtct cggtgtcgcc gctgcatggc    840
gtcaatcgct atatcaagga aatcgaggac cgcttgctgg ccttgctgtt gttgttgctg    900
atcagcccgt tgatgctggt cattgcgctt ggcgtgaaac tgagttctcc gggcccggtg    960 tttacaagc aggtcagagt gggctggaac aatcgcaaat tcacgatgct gaagtttcgt   1020
tcgatgccgg tcgatgccga ggccaaaacc ggcgcggtct gggccaggcc cggcgaaaac   1080
cgtgcaaccc ggtttggggc cttcctgcgc aaaaccagtc tggacgagtt gccgcagttg   1140
atcaatgtgc tcaagggcga catgtcgctg tcggcccgc gccctgaacg gcccgatttc   1200
gtcgaggtgt tcaaggatca agtacccaat tacatgaaaa acacatggt caaggcgggc   1260 attaccggtt gggcacaagt caacggctgg cgcggtgata ccgacctgaa tcgccgcatc   1320
gaacacgatc tgtattacat ccagcattgg tcggtctggt tcgatctgga gattgccttt   1380
cgcaccgtgt tgaccggctt tatcaacaaa aatgcctat                          1419
```

<210> SEQ ID NO 4
<211> LENGTH: 473
<212> TYPE: PRT
<213> ORGANISM: Methylomonas 16a

<400> SEQUENCE: 4

```
Met Pro Leu Gly Leu Gly Asn Ile Phe Asn Gly Leu Phe Lys Gln Tyr
  1               5                  10                  15

Gly His Thr Val Ile Leu Leu Arg Val Ile Asp Val Val Met Leu
                 20                  25                  30

Leu Gly Ala Ala Trp Leu Ala His Tyr Phe Trp Leu His Asp Ser Val
             35                  40                  45

Ile Asp Gln His Tyr Arg Phe Val Ile Ala Leu Gly Ile Leu Gly Ala
         50                  55                  60

Ile Ile Phe Phe Glu Ile Gly Gln Val Tyr Arg Pro Trp Arg Asn Asp
 65                  70                  75                  80

Ala Met Arg Gly Glu Ile Pro Arg Ile Ile Arg Ala Trp Leu Leu Ala
                 85                  90                  95

Leu Leu Thr Val Val Ser Ile Val Ala Leu Val Arg Leu His Phe Trp
            100                 105                 110

Phe Gly Ser Ser Tyr Arg Trp Ile Ala Ser Trp Gly Gly Leu Gly Leu
        115                 120                 125

Phe Phe Val Leu Ala Ala Arg Gly Val Leu Ala Gln Val Leu Lys Trp
    130                 135                 140

Leu Arg Ala Arg Gly Trp Ser Gln Gly Arg Ile Ile Leu Val Gly Leu
145                 150                 155                 160
```

```
Asn Gln Met ala Val Ala Val Ser Arg Gln Leu Asn His Ser Ser Trp
            165                 170                 175
Ala Gly Leu Gln Val Ile Gly Tyr Val Asp Asp Arg Ala Glu Asp Arg
            180                 185                 190
Leu Ala Val Ala Asp Tyr Ser Leu Pro Arg Leu Gly Lys Leu Ser Asp
            195                 200                 205
Leu Pro Arg Leu Val Ser Arg Gln Ala Val Asp Glu Val Trp Val Ala
    210                 215                 220
Phe Pro Gly Ala Ser Leu Ala Glu Arg Val Gln His Glu Leu Arg His
225                 230                 235                 240
Leu Pro Val Ser Ile Arg Leu Val Ile Asp Cys Phe Ala Phe Lys Gln
            245                 250                 255
Ser Lys Phe Leu Ser Leu Asn Thr Val Ala Gly Ile Pro Thr Leu Asp
            260                 265                 270
Val Ser Val Ser Pro Leu His Gly Val Asn Arg Tyr Ile Lys Glu Ile
            275                 280                 285
Glu Asp Arg Leu Leu Ala Leu Leu Leu Leu Ile Ser Pro Leu
    290                 295                 300
Met Leu Val Ile Ala Leu Gly Val Lys Leu Ser Ser Pro Gly Pro Val
305                 310                 315                 320
Phe Tyr Lys Gln Val Arg Val Gly Trp Asn Asn Arg Lys Phe Thr Met
            325                 330                 335
Leu Lys Phe Arg Ser Met Pro Val Asp Ala Glu Ala Lys Thr Gly Ala
            340                 345                 350
Val Trp Ala Arg Pro Gly Glu Asn Arg Ala Thr Arg Phe Gly Ala Phe
            355                 360                 365
Leu Arg Lys Thr Ser Leu Asp Glu Leu Pro Gln Leu Ile Asn Val Leu
    370                 375                 380
Lys Gly Asp Met Ser Leu Val Gly Pro Arg Pro Glu Arg Pro Asp Phe
385                 390                 395                 400
Val Glu Val Phe Lys Asp Gln Val Pro Asn Tyr Met Lys Lys His Met
            405                 410                 415
Val Lys Ala Gly Ile Thr Gly Trp Ala Gln Val Asn Gly Trp Arg Gly
            420                 425                 430
Asp Thr Asp Leu Asn Arg Arg Ile Glu His Asp Leu Tyr Tyr Ile Gln
            435                 440                 445
His Trp Ser Val Trp Phe Asp Leu Glu Ile Ala Phe Arg Thr Val Leu
    450                 455                 460
Thr Gly Phe Ile Asn Lys Asn Ala Tyr
465                 470
```

<210> SEQ ID NO 5
<211> LENGTH: 1098
<212> TYPE: DNA
<213> ORGANISM: Methylomonas 16a

<400> SEQUENCE: 5

```
atgtttagac taattcccat catgctggtt ttactgttgc caggctgttt cctggcaccg      60
ggtatggata tgcagaccga tggcgacttg acagaaatcg agctgccaac catgaagggc     120
gggcagttgg tcaaggagaa acccgcatt cagccgatca ccgccgattt gatcatcgag      180
cgtgaagtcg cacggcggca agccgtcaac aatctaccgc cgatggacga aacccggacc     240
agttatcgca tcggtccgca ggacaggttg caaatcacgg tatgggagca tcccgaactg     300
```

-continued

```
aacgatcccg gcggcgagaa aatcctgccg gaactggccg gcaaggtcgt ggacgataac    360
ggcgatttgt attaccccta tgtcggtacc cttcatgtcg gcggcaagac cgtcaccgaa    420
gtgcgcgagg aattgacccg cgaactgtcc aaatacttca aaaaggtcaa actcgacatt    480
cgtgtgctgt cgttccaggc tcaccgcgtc gcggtggtcg gtgaagtcag aaatcccggc    540
atcgtcgcga tgaccgaaac gccgttgacg gtggcagaag ccatcagcag ggccggcggc    600
gccacgcaag attccgattt gaacaacgtc gcgctggccc gcggcggccg gttgtacaaa    660
ctggatgtgc aagccttgta tgaaaaaggc ctgaccacgc aaaacctgct gttgcgggat    720
ggcgatgtgc tgaacgtcgg cgatcagaaa gacagcaagg tttatgtgat gggcgaggtc    780
ggccggcagc aggccatcca gatcaacaag gccggatgat gtctggctca ggcgctggcc    840
gaagcctatg gcgtcgattt caacacctcg cgtcccggcg atatttacgt gctgcgcgcc    900
ggcgacatgc agccggagat tttccagctg acgccgaatc gcccgacgc gatgatcctg    960 gccgagcaat tcccgttgca gccgcacgac acgctattcg tcggtacggc cggggtcacg    1020
caatggtcca gggtgctgaa tcagattctg ccgggttcgt ttaccgccat catgtcgcaa    1080
gccgcgatga tggggatg                                                  1098
```

<210> SEQ ID NO 6
<211> LENGTH: 366
<212> TYPE: PRT
<213> ORGANISM: Methylomonas 16a

<400> SEQUENCE: 6

```
Met Phe Arg Leu Ile Pro Ile Met Leu Val Leu Leu Pro Gly Cys
  1               5                  10                  15

Phe Leu Ala Pro Gly Met Asp Met Gln Thr Asp Gly Asp Leu Thr Glu
                 20                  25                  30

Ile Glu Leu Pro Thr Met Lys Gly Gly Gln Leu Val Lys Glu Lys Thr
            35                  40                  45

Arg Ile Gln Pro Ile Thr Ala Asp Leu Ile Ile Glu Arg Glu Val Ala
     50                  55                  60

Arg Arg Gln Ala Val Asn Asn Leu Pro Pro Met Asp Glu Thr Arg Thr
 65                  70                  75                  80

Ser Tyr Arg Ile Gly Pro Gln Asp Arg Leu Gln Ile Thr Val Trp Glu
                 85                  90                  95

His Pro Glu Leu Asn Asp Pro Gly Gly Glu Lys Ile Leu Pro Glu Leu
            100                 105                 110

Ala Gly Lys Val Val Asp Asp Asn Gly Asp Leu Tyr Tyr Pro Tyr Val
        115                 120                 125

Gly Thr Leu His Val Gly Gly Lys Thr Val Thr Glu Val Arg Glu Glu
    130                 135                 140

Leu Thr Arg Glu Leu Ser Lys Tyr Phe Lys Lys Val Lys Leu Asp Ile
145                 150                 155                 160

Arg Val Leu Ser Phe Gln Ala His Arg Val Ala Val Gly Glu Val
                165                 170                 175

Arg Asn Pro Gly Ile Val Ala Met Thr Glu Thr Pro Leu Thr Val Ala
            180                 185                 190

Glu Ala Ile Ser Arg Ala Gly Gly Ala Thr Gln Asp Ser Asp Leu Asn
        195                 200                 205

Asn Val Ala Leu Ala Arg Gly Gly Arg Leu Tyr Lys Leu Asp Val Gln
    210                 215                 220

Ala Leu Tyr Glu Lys Gly Leu Thr Thr Gln Asn Leu Leu Leu Arg Asp
```

|     |     |     |     | 225 |     |     |     | 230 |     |     |     | 235 |     |     |     | 240 |
| --- | --- | --- | --- | --- | --- | --- | --- | --- | --- | --- | --- | --- | --- | --- | --- | --- |

Gly Asp Val Leu Asn Val Gly Asp Gln Lys Asp Ser Lys Val Tyr Val
                          245                        250                255

Met Gly Glu Val Gly Arg Gln Gln Ala Ile Gln Ile Asn Lys Gly Arg
         260                   265                   270

Met Ser Leu Ala Gln Ala Leu Ala Glu Ala Tyr Gly Val Asp Phe Asn
        275                   280                 285

Thr Ser Arg Pro Gly Asp Ile Tyr Val Leu Arg Ala Gly Asp Met Gln
   290                   295                   300

Pro Glu Ile Phe Gln Leu Asp Ala Glu Ser Pro Asp Ala Met Ile Leu
305                    310                   315               320

Ala Glu Gln Phe Pro Leu Gln Pro His Asp Thr Leu Phe Val Gly Thr
             325                 330                 335

Ala Gly Val Thr Gln Trp Ser Arg Val Leu Asn Gln Ile Leu Pro Gly
           340                   345                350

Ser Phe Thr Ala Ile Met Ser Gln Ala Ala Met Met Gly Met
              355                 360                365

<210> SEQ ID NO 7
<211> LENGTH: 2337
<212> TYPE: DNA
<213> ORGANISM: Methylomonas 16a

<400> SEQUENCE: 7

```
atgccgccct tgaatcccgt gatgatgcag gagcctggcg tcagcatccg cgattatgtc      60
gatctgttga tcgagggcaa gaagacaata ctgttgacgt tggccatcgt gctgagcgtg     120
acgatgattt atttggtttt ggccccgcgc acttacaagg ccgatgcctt gctgcgtatc     180
gacaaaaata agccttgtt ggcggccaat ttgcgtagcg agggcaatgg tacgccaacg     240
gaggcggaaa accccaggc gcaacgggaa gtggaaattt gccgctcgcg ttcggtgctg     300
ggcaaggtgg tggaggattt gaatctagtc gtggaggcgt cgccacgata ctttcccatc     360
atcggcgaaa ccctggcccg caagcacgac aaacatgagg gcgtagccgg cgcctggtgg     420
ggattcagcc gttgggcctg ggcggggaa aaactgaaaa tcgagcgttt cgaggtgccc     480
gatcgttacc tggacaaggc ttttactttg gtggcgctgg aagcagggcg ttttcaatta     540
ttgagcccta agggcgaggt gctggccgaa ggtttgctcg gtgaaacgct gaccgccgac     600
atcggcgaag ccagtcccgt cgtcgtcaac gtcgctgatt gcaggcgca ttacggcacc     660
gagttcgagt tgcggcgcaa acctcgctg gcggccatag aaaccctgca aaaagccttt     720
tcggtcaagg aagtgtccaa ggataccaat attctgagtg tcgaactcaa ggggcgcgat     780
cccgagcaat tggccaaatc ggtcaacgac atcgccagta tttacgtcaa cgccacggtg     840
aattgggaat cggcggaagc ctcgcaaaag ctgaatttcc tggagagcca gttgccgctg     900
gtgaaggaga atctggaaaa ggctgagcaa gccttgagcg cttaccggca gcaacatggc     960
gcggtggata tttccgccga agccgaaatc ctgctgaaac aggcctcgga atgaaaacc    1020
ttgagcatac aactcaagca aaagtacgac gagcaaagcc agcgtctgga atcggagcat    1080
ccggacatga tcgccaccaa tgcgcaaatc cgccgggtga gcaataaatt ggcggccttg    1140
gaaaagcgca tcaaggactt gccgaagacg cagcaaaaca tggtcagcct gtcgcgcgat    1200
gtgcaggtca ataccgagct ttacacctcg ttgctgaaca cgcgcaggga gcaacgcatc    1260
gccgcggccg gttccctggg taattcgcgc atcgtcgatt tcgcggtggt tccggaaaaa    1320
ccttattggc ccaagcccgg tttgctgttg gcgattgccg gtttgctggg catcagtctg    1380
```

-continued

```
ggttcggcgc tgatattcct gagacattcg ttgcagcgcc atgacaatta tccggccttg   1440
ctggaatacc aggtcggctt gccgctgttc gccgccattc cgcacagcaa gaaacaaaga   1500
cgcttggcac gcctgctgga tcagggcaag gagcgggata ccgcgattct ggtcagccac   1560
gatccgctgg atatttcggt cgaatccttg cgcggcttgc gcactacgct ggaagcgacg   1620
ctggccagcg atgaaagcaa ggtcatcatg gtcagcagtc cggcgccggg catgggtaaa   1680
tccttcatca gcaccaattt ggcggctctg ttggccagca tacgcaagcg ggtgctgatc   1740
atcgacgccg acatgcgcaa cggccgcctg catgaaacct ttgccattgc caagcaaccg   1800
ggcttgtccg atctgctgtc cggcaaggtc agcctgggcg acgtgatcgt cagtttgccg   1860
gagataggcg tggatttgat tcccaggggc gagatggtgc tgaatccggc cgaattgttg   1920
gtgctgggcg atctggccga taccttggag caactgaaga gcttttacaa ccatatcgtc   1980
atcgattcgc cgccgatctt gggcgccacc gacgcggcga tcatgggcaa gcattgcgat   2040
gctaccttcc tggtggtcaa ggagggccgt tataccgcgc aagagctgga ggtcagtttc   2100
aggcgcttgc agcaagtcgg cgtgaaaccc aacggtttca tcatcaacga catgaaggaa   2160
ggttcgtcct attcccgta ctacggctat gcctatcagc gggatgacat gcgacaaaaa   2220
caaaccacgg cttggcaggc gcgctttcaa aacctgaatg actggatggg gcggcaggac   2280
gccgagtatt tacccgtcgc cgacgacgcg gaagaacttc acgacagcat cagggcc     2337

<210> SEQ ID NO 8
<211> LENGTH: 779
<212> TYPE: PRT
<213> ORGANISM: Methylomonas 16a

<400> SEQUENCE: 8

Met Pro Pro Leu Asn Pro Val Met Met Gln Glu Pro Gly Val Ser Ile
  1               5                  10                  15

Arg Asp Tyr Val Asp Leu Leu Ile Glu Gly Lys Lys Thr Ile Leu Leu
                 20                  25                  30

Thr Leu Ala Ile Val Leu Ser Val Thr Met Ile Tyr Leu Val Leu Ala
             35                  40                  45

Pro Arg Thr Tyr Lys Ala Asp Ala Leu Leu Arg Ile Asp Lys Asn Lys
         50                  55                  60

Ala Leu Leu Ala Ala Asn Leu Arg Ser Glu Gly Asn Gly Thr Pro Thr
 65                  70                  75                  80

Glu Ala Glu Asn Pro Arg Ala Gln Arg Glu Val Ile Leu Arg Ser
                 85                  90                  95

Arg Ser Val Leu Gly Lys Val Val Glu Asp Leu Asn Leu Val Val Glu
                100                 105                 110

Ala Ser Pro Arg Tyr Phe Pro Ile Ile Gly Glu Thr Leu Ala Arg Lys
            115                 120                 125

His Asp Lys His Glu Gly Val Ala Gly Ala Trp Trp Gly Phe Ser Arg
        130                 135                 140

Trp Ala Trp Gly Gly Glu Lys Leu Lys Ile Glu Arg Phe Glu Val Pro
145                 150                 155                 160

Asp Arg Tyr Leu Asp Lys Ala Phe Thr Leu Val Ala Leu Glu Ala Gly
                165                 170                 175

Arg Phe Gln Leu Leu Ser Pro Lys Gly Glu Val Leu Ala Glu Gly Leu
            180                 185                 190

Leu Gly Glu Thr Leu Thr Ala Asp Ile Gly Glu Ala Ser Pro Val Val
        195                 200                 205
```

-continued

Val Asn Val Ala Asp Leu Gln Ala His Tyr Gly Thr Glu Phe Glu Leu
    210                 215                 220

Arg Arg Lys Thr Ser Leu Ala Ala Ile Glu Thr Leu Gln Lys Ala Phe
225                 230                 235                 240

Ser Val Lys Glu Val Ser Lys Asp Thr Asn Ile Leu Ser Val Glu Leu
                245                 250                 255

Lys Gly Arg Asp Pro Glu Gln Leu Ala Lys Ser Val Asn Asp Ile Ala
            260                 265                 270

Ser Ile Tyr Val Asn Ala Thr Val Asn Trp Glu Ser Ala Glu Ala Ser
        275                 280                 285

Gln Lys Leu Asn Phe Leu Glu Ser Gln Leu Pro Leu Val Lys Glu Asn
    290                 295                 300

Leu Glu Lys Ala Glu Gln Ala Leu Ser Ala Tyr Arg Gln Gln His Gly
305                 310                 315                 320

Ala Val Asp Ile Ser Ala Glu Ala Glu Ile Leu Leu Lys Gln Ala Ser
                325                 330                 335

Glu Met Glu Thr Leu Ser Ile Gln Leu Lys Gln Lys Tyr Asp Glu Gln
            340                 345                 350

Ser Gln Arg Leu Glu Ser Glu His Pro Asp Met Ile Ala Thr Asn Ala
        355                 360                 365

Gln Ile Arg Arg Val Ser Asn Lys Leu Ala Ala Leu Glu Lys Arg Ile
    370                 375                 380

Lys Asp Leu Pro Lys Thr Gln Gln Asn Met Val Ser Leu Ser Arg Asp
385                 390                 395                 400

Val Gln Val Asn Thr Glu Leu Tyr Thr Ser Leu Leu Asn Ser Ala Gln
                405                 410                 415

Glu Gln Arg Ile Ala Ala Ala Gly Ser Leu Gly Asn Ser Arg Ile Val
            420                 425                 430

Asp Phe Ala Val Val Pro Glu Lys Pro Tyr Trp Pro Lys Pro Gly Leu
        435                 440                 445

Leu Leu Ala Ile Ala Gly Leu Leu Gly Ile Ser Leu Gly Ser Ala Leu
    450                 455                 460

Ile Phe Leu Arg His Ser Leu Gln Arg His Asp Asn Tyr Pro Ala Leu
465                 470                 475                 480

Leu Glu Tyr Gln Val Gly Leu Pro Leu Phe Ala Ala Ile Pro His Ser
                485                 490                 495

Lys Lys Gln Arg Arg Leu Ala Arg Leu Leu Asp Gln Gly Lys Glu Arg
            500                 505                 510

Asp Thr Ala Ile Leu Val Ser His Asp Pro Leu Asp Ile Ser Val Glu
        515                 520                 525

Ser Leu Arg Gly Leu Arg Thr Thr Leu Glu Ala Thr Leu Ala Ser Asp
    530                 535                 540

Glu Ser Lys Val Ile Met Val Ser Ser Pro Ala Pro Gly Met Gly Lys
545                 550                 555                 560

Ser Phe Ile Ser Thr Asn Leu Ala Ala Leu Ala Ser Ile Arg Lys
                565                 570                 575

Arg Val Leu Ile Ile Asp Ala Asp Met Arg Asn Gly Arg Leu His Glu
            580                 585                 590

Thr Phe Ala Ile Ala Lys Gln Pro Gly Leu Ser Asp Leu Leu Ser Gly
        595                 600                 605

Lys Val Ser Leu Gly Asp Val Ile Val Ser Leu Pro Glu Ile Gly Val
    610                 615                 620

-continued

Asp Leu Ile Pro Arg Gly Glu Met Val Leu Asn Pro Ala Glu Leu Leu
625                 630                 635                 640

Val Leu Gly Asp Leu Ala Asp Thr Leu Glu Gln Leu Lys Ser Phe Tyr
            645                 650                 655

Asn His Ile Val Ile Asp Ser Pro Pro Ile Leu Gly Ala Thr Asp Ala
        660                 665                 670

Ala Ile Met Gly Lys His Cys Asp Ala Thr Phe Leu Val Val Lys Glu
    675                 680                 685

Gly Arg Tyr Thr Ala Gln Glu Leu Glu Val Ser Phe Arg Arg Leu Gln
690                 695                 700

Gln Val Gly Val Lys Pro Asn Gly Phe Ile Ile Asn Asp Met Lys Glu
705                 710                 715                 720

Gly Ser Ser Tyr Tyr Pro Tyr Tyr Gly Tyr Ala Tyr Gln Arg Asp Asp
            725                 730                 735

Met Arg Gln Lys Gln Thr Thr Ala Trp Gln Ala Arg Phe Gln Asn Leu
        740                 745                 750

Asn Asp Trp Met Gly Arg Gln Asp Ala Glu Tyr Leu Pro Val Ala Asp
        755                 760                 765

Asp Ala Glu Glu Leu His Asp Ser Ile Arg Ala
770                 775

<210> SEQ ID NO 9
<211> LENGTH: 1416
<212> TYPE: DNA
<213> ORGANISM: Methylomonas 16a

<400> SEQUENCE: 9

```
atgttgggca aagggcattc ggacaaggct aatttaaagg aaggtttcat gctggattgg     60
ttgaggcaaa agaacttgtt gggtgacgcc tgttgggcgc tggcgggaca gttattgtcg    120
gcactggctt gcttgcgggg cacgcgcatc ctgaccgaat ggtgacgcc ggcggttttc    180
gggcacgtgg cgttgctgaa tggcttcgtc gcgctggggg tggcggtgtt tgcctatccc    240
ttcatctgcg ccgggatgcg tttcaccaat gaatgccgaa atttccgcga gcgggcggca    300
ttgcatggat tggtgtttgc gctgacgacg cgatcgacgg cattggccat taccttgctg    360
ctgctgggcg cgcgctgta ttgctatttt gtcggtagtg aaatcggctt gttcgtgttg    420
accggattgc tgttagccgt caccgttcgc cgcgagttgg gcattcagct gatgataggc    480
gaacgcaagc aacgcggcgc cgcgcttttgg caaaccagcg acagcatcct gcggccggtg    540
atggcgattt ggctggtatg gggtttgggg caaagtccgg aagcggtgtt gttgggctat    600
gtctgtgcca gcgtgctggc caatacgctg tggacgatcg taagcgatgc atggcaaaaa    660
aagcctaccg gcgatcgcgg cttcctgggg cggcaattcg agcgcggcct ttgggcttat    720
gccttgccgt tgatcccgat ggaattgatg ttctggctca acggcctggg cgaccgttac    780
gtgatcggtt atttcctaac ggcggctgaa gtgggggtgt acgcggccgc ttatacgctg    840
gtcaacgaag ccttcaatcg tagcgcgatg tgttgttgc gcacgtttca gccggcctat    900
tttcaagcgg tttcccaagg caaaagcaaa gatgcatgtt cgctgctatg gctgtggata    960
gggggcggtcg tcgtgatgag tgttctgggc gtgacgctgg tctggttgtg caaggactgg   1020
ctggtcgcag gcttgttggc agaaccctat catgcggccg gcgcgctgat gccggttatc   1080
gccgcgggca cggccttgca tgccctgggc accgtgatgt cccagccgct gctggcgaga   1140
aaacgcacgc cgatcttgct gcgcgggcgt atctgtgggc gttggcggc gctcatcacg   1200
ctgccttgc tggtggcgca ttttggcctg ttcggggcgg ccttggccaa tccgtatat   1260
```

-continued

```
ttcggcatcg aagcgctggt gttggccttg ctggccaagc cctggcgcaa gctccgcacg      1320
ggacggcagg cgcggatcgt tcaatccgaa gcggcgatgc ccgaacccga ctttgacgcc      1380
atcggagtga gagcggcggc gttctccaac gaatcc                                1416

<210> SEQ ID NO 10
<211> LENGTH: 472
<212> TYPE: PRT
<213> ORGANISM: Methylomonas 16a

<400> SEQUENCE: 10

Met Leu Gly Lys Gly His Ser Asp Lys Ala Asn Leu Lys Glu Gly Phe
 1               5                  10                  15

Met Leu Asp Trp Leu Arg Gln Lys Asn Leu Leu Gly Asp Ala Cys Trp
             20                  25                  30

Ala Leu Ala Gly Gln Leu Leu Ser Ala Leu Ala Leu Ala Gly Thr
         35                  40                  45

Arg Ile Leu Thr Glu Leu Val Thr Pro Ala Val Phe Gly His Val Ala
     50                  55                  60

Leu Leu Asn Gly Phe Val Ala Leu Gly Val Ala Val Phe Ala Tyr Pro
 65                  70                  75                  80

Phe Ile Cys Ala Gly Met Arg Phe Thr Asn Glu Cys Arg Asn Phe Arg
                 85                  90                  95

Glu Arg Ala Ala Leu His Gly Leu Val Phe Ala Leu Thr Thr Arg Ser
            100                 105                 110

Thr Ala Leu Ala Ile Thr Leu Leu Leu Gly Gly Ala Leu Tyr Cys
        115                 120                 125

Tyr Phe Val Gly Ser Glu Ile Gly Leu Phe Val Leu Thr Gly Leu Leu
    130                 135                 140

Leu Ala Val Thr Val Arg Arg Glu Leu Gly Ile Gln Leu Met Ile Gly
145                 150                 155                 160

Glu Arg Lys Gln Arg Gly Ala Ala Leu Trp Gln Thr Ser Asp Ser Ile
                165                 170                 175

Leu Arg Pro Val Met ala Ile Trp Leu Val Trp Gly Leu Gly Gln Ser
            180                 185                 190

Pro Glu Ala Val Leu Leu Gly Tyr Val Cys Ala Ser Val Leu Ala Asn
        195                 200                 205

Thr Leu Trp Thr Ile Val Ser Asp Ala Trp Gln Lys Lys Pro Thr Gly
    210                 215                 220

Asp Arg Gly Phe Leu Gly Arg Gln Phe Glu Arg Gly Leu Trp Ala Tyr
225                 230                 235                 240

Ala Leu Pro Leu Ile Pro Met Glu Leu Met Phe Trp Leu Asn Gly Leu
                245                 250                 255

Gly Asp Arg Tyr Val Ile Gly Tyr Phe Leu Thr Ala Ala Glu Val Gly
            260                 265                 270

Val Tyr Ala Ala Ala Tyr Thr Leu Val Asn Glu Ala Phe Asn Arg Ser
        275                 280                 285

Ala Met Val Leu Leu Arg Thr Phe Gln Pro Ala Tyr Phe Gln Ala Val
    290                 295                 300

Ser Gln Gly Lys Ser Lys Asp Ala Cys Ser Leu Leu Trp Leu Trp Ile
305                 310                 315                 320

Gly Ala Val Val Met Ser Val Leu Gly Val Thr Leu Val Trp Leu
                325                 330                 335

Cys Lys Asp Trp Leu Val Ala Gly Leu Leu Ala Glu Pro Tyr His Ala
```

```
            340                 345                 350
Ala Gly Ala Leu Met Pro Val Ile Ala Ala Gly Thr Ala Leu His Ala
            355                 360                 365
Leu Gly Thr Val Met Ser Gln Pro Leu Leu Ala Arg Lys Arg Thr Pro
        370                 375                 380
Ile Leu Leu Arg Gly Arg Ile Cys Gly Ala Leu Ala Ala Leu Ile Thr
385                 390                 395                 400
Leu Pro Leu Leu Val Ala His Phe Gly Leu Phe Gly Ala Ala Leu Ala
                405                 410                 415
Asn Pro Val Tyr Phe Gly Ile Glu Ala Leu Val Leu Ala Leu Leu Ala
                420                 425                 430
Lys Pro Trp Arg Lys Leu Arg Thr Gly Arg Gln Ala Arg Ile Val Gln
            435                 440                 445
Ser Glu Ala Ala Met Pro Glu Pro Asp Phe Asp Ala Ile Gly Val Arg
        450                 455                 460
Ala Ala Ala Phe Ser Asn Glu Ser
465                 470
```

<210> SEQ ID NO 11
<211> LENGTH: 816
<212> TYPE: DNA
<213> ORGANISM: Methylomonas 16a

<400> SEQUENCE: 11

```
ccgataaaca ggtgtgaacc attgaacagc ttgaccatag tcattttgac gctgaacgag    60
gccgccaatc tgccccggtg cctggcggcg attccgcaac gttaccctgt cgtgatcttg   120
gattccggga gcagcgatga cacgctgtcg atcgcggaag ccacggctg caagatttat   180
caaaatcctt ggcccggctt tgccgagcag cgcaattttg cgttgaatca atgcgatatc   240
gagacgccgt gggtgttgtt cgtcgatgcc gacgaaatct acccgcaagt cttttatcag   300
catttcgaca gtggaatgct gcaaaccgga gagatcgatg tgctgatggt gccgtccatt   360
ttgttttttgc gcggcaaacg cctgcatcat gcgccgggtt atccgatcta tcacccgcgc   420
ctggttcggc gggaaacgac ccgcttcgtg cgtaatcata ccggtcacgg cgaggccgtc   480
atggatagtt gccgcatcgg ctacaccgat attccctatg atcattactt ttacgacggc   540
gagatcatcc agtggatgca taagcatgtc gacaaagccg ctcaggaagt tcggctcaaa   600
ccgacccagg gcgcgttgat gacgacccgc gggcgcttga gcgtaatgct ggggcgttca   660
tggagccgaa tcctggccag gtttgtttac cactatctgc tgcgcggcgg cttttttggac   720
ggcgcggcgg gattggaatt tacgctgatg tttacctggt atgaagccag catctatctg   780
caagccaaag ccgctgcaca agcaagggga acagca                             816
```

<210> SEQ ID NO 12
<211> LENGTH: 272
<212> TYPE: PRT
<213> ORGANISM: Methylomonas 16a

<400> SEQUENCE: 12

```
Pro Ile Asn Arg Cys Glu Pro Leu Asn Ser Leu Thr Ile Val Ile Leu
1               5                   10                  15
Thr Leu Asn Glu Ala Ala Asn Leu Pro Arg Cys Leu Ala Ala Ile Pro
                20                  25                  30
Gln Arg Tyr Pro Val Val Ile Leu Asp Ser Gly Ser Ser Asp Asp Thr
            35                  40                  45
```

```
Leu Ser Ile Ala Glu Gly His Gly Cys Lys Ile Tyr Gln Asn Pro Trp
 50                  55                  60

Pro Gly Phe Ala Glu Gln Arg Asn Phe Ala Leu Asn Gln Cys Asp Ile
 65                  70                  75                  80

Glu Thr Pro Trp Val Leu Phe Val Asp Ala Asp Glu Ile Tyr Pro Gln
                 85                  90                  95

Val Phe Tyr Gln His Phe Asp Ser Gly Met Leu Gln Thr Gly Glu Ile
            100                 105                 110

Asp Val Leu Met Val Pro Ser Ile Leu Phe Leu Arg Gly Lys Arg Leu
            115                 120                 125

His His Ala Pro Gly Tyr Pro Ile Tyr His Pro Arg Leu Val Arg Arg
        130                 135                 140

Glu Thr Thr Arg Phe Val Arg Asn His Thr Gly His Gly Glu Ala Val
145                 150                 155                 160

Met Asp Ser Cys Arg Ile Gly Tyr Thr Asp Ile Pro Tyr Asp His Tyr
                165                 170                 175

Phe Tyr Asp Gly Glu Ile Ile Gln Trp Met His Lys His Val Asp Lys
            180                 185                 190

Ala Ala Gln Glu Val Arg Leu Lys Pro Thr Gln Gly Ala Leu Met Thr
        195                 200                 205

Thr Arg Gly Arg Leu Ser Val Met Leu Gly Arg Ser Trp Ser Arg Ile
210                 215                 220

Leu Ala Arg Phe Val Tyr His Tyr Leu Leu Arg Gly Gly Phe Leu Asp
225                 230                 235                 240

Gly Ala Ala Gly Leu Glu Phe Thr Leu Met Phe Thr Trp Tyr Glu Ala
                245                 250                 255

Ser Ile Tyr Leu Gln Ala Lys Ala Ala Ala Gln Ala Arg Gly Thr Ala
            260                 265                 270

<210> SEQ ID NO 13
<211> LENGTH: 852
<212> TYPE: DNA
<213> ORGANISM: Methylomonas 16a

<400> SEQUENCE: 13
atgaaagtgt cattgatatt ggctacgctc ggcagggacc tggaactgct ggattttttg     60
aaatccttgc tgtttcagac ctacaagaac ttcgagttga tcgtcatcga ccagaatcaa    120
gacggcaaaa tcgatcggat tgccgagcaa tatagccaat gcctcgatct gaaacacgtc    180
aaggtgaatt tcaccggtaa tgcccgagcc agggatcatg catcgccctt ggcccagggc    240
gacatcatcg cctttccgga cgatgattgc gtgtatgaaa aggatgtgct ggaaaaagtg    300
gtaggcgaat ttgcatgcca gccaacgttg tcgattctgg tagccgggtc ctacgatttt    360
tccgcgaaac acttcagcat aggcgtcaac agccgtaaag cgcgttattt ttcccggttg    420
aacatgatgg gggtggagtt cacgcagttt tttgcgctgg cgcgtatcga caggcggcag    480
ttttatttgg accacgattt cggcatcggc tccaaatatg ccggggcgga aggcttcgag    540
ttgctgtatc gcctgctgcg cgcgggcggg cgggcgttct acaagccgga tatcaaaatc    600
tatcacgcca acaaggacca ttacacgctg gtaccgcgc gcatgctgaa atattccacc     660
ggtattggcg cctatatccg caaattcgcc aatcagcatg atccctatat cggctattac    720
atcctgcgca agatgctgat agccccgact ctgaaaatgc tgctggcctt gttgacgttc    780
aacccgggaa aactcgccta ttcgttttat aacctggtgg gcatatggcg cggatttttt    840
gcctatgggc gc                                                         852
```

<210> SEQ ID NO 14
<211> LENGTH: 284
<212> TYPE: PRT
<213> ORGANISM: Methylomonas 16a

<400> SEQUENCE: 14

| Met | Lys | Val | Ser | Leu | Ile | Leu | Ala | Thr | Leu | Gly | Arg | Asp | Leu | Glu | Leu |
|---|---|---|---|---|---|---|---|---|---|---|---|---|---|---|---|
| 1 | | | | 5 | | | | | 10 | | | | | 15 | |

| Leu | Asp | Phe | Leu | Lys | Ser | Leu | Leu | Phe | Gln | Thr | Tyr | Lys | Asn | Phe | Glu |
|---|---|---|---|---|---|---|---|---|---|---|---|---|---|---|---|
| | | | | 20 | | | | | 25 | | | | | 30 | |

| Leu | Ile | Val | Ile | Asp | Gln | Asn | Gln | Asp | Gly | Lys | Ile | Asp | Arg | Ile | Ala |
|---|---|---|---|---|---|---|---|---|---|---|---|---|---|---|---|
| | | | 35 | | | | | 40 | | | | | 45 | | |

| Glu | Gln | Tyr | Ser | Gln | Cys | Leu | Asp | Leu | Lys | His | Val | Lys | Val | Asn | Phe |
|---|---|---|---|---|---|---|---|---|---|---|---|---|---|---|---|
| | 50 | | | | | 55 | | | | | 60 | | | | |

| Thr | Gly | Asn | Ala | Arg | Ala | Arg | Asp | His | Gly | Ile | Ala | Leu | Ala | Gln | Gly |
|---|---|---|---|---|---|---|---|---|---|---|---|---|---|---|---|
| 65 | | | | | 70 | | | | | 75 | | | | | 80 |

| Asp | Ile | Ile | Ala | Phe | Pro | Asp | Asp | Cys | Val | Tyr | Glu | Lys | Asp | Val |
|---|---|---|---|---|---|---|---|---|---|---|---|---|---|---|
| | | | | 85 | | | | | 90 | | | | | 95 |

| Leu | Glu | Lys | Val | Val | Gly | Glu | Phe | Ala | Cys | Gln | Pro | Thr | Leu | Ser | Ile |
|---|---|---|---|---|---|---|---|---|---|---|---|---|---|---|---|
| | | | | 100 | | | | | 105 | | | | | 110 | |

| Leu | Val | Ala | Gly | Ser | Tyr | Asp | Phe | Ser | Ala | Lys | His | Phe | Ser | Ile | Gly |
|---|---|---|---|---|---|---|---|---|---|---|---|---|---|---|---|
| | | | 115 | | | | | 120 | | | | | 125 | | |

| Val | Asn | Ser | Arg | Lys | Ala | Arg | Tyr | Phe | Ser | Arg | Leu | Asn | Met | Met | Gly |
|---|---|---|---|---|---|---|---|---|---|---|---|---|---|---|---|
| | 130 | | | | | 135 | | | | | 140 | | | | |

| Val | Glu | Phe | Thr | Gln | Phe | Phe | Ala | Leu | Ala | Arg | Ile | Asp | Arg | Arg | Gln |
|---|---|---|---|---|---|---|---|---|---|---|---|---|---|---|---|
| 145 | | | | | 150 | | | | | 155 | | | | | 160 |

| Phe | Tyr | Leu | Asp | His | Asp | Phe | Gly | Ile | Gly | Ser | Lys | Tyr | Ala | Gly | Ala |
|---|---|---|---|---|---|---|---|---|---|---|---|---|---|---|---|
| | | | | 165 | | | | | 170 | | | | | 175 | |

| Glu | Gly | Phe | Glu | Leu | Leu | Tyr | Arg | Leu | Leu | Arg | Ala | Gly | Gly | Arg | Ala |
|---|---|---|---|---|---|---|---|---|---|---|---|---|---|---|---|
| | | | 180 | | | | | 185 | | | | | 190 | | |

| Phe | Tyr | Lys | Pro | Asp | Ile | Lys | Ile | Tyr | His | Ala | Asn | Lys | Asp | His | Tyr |
|---|---|---|---|---|---|---|---|---|---|---|---|---|---|---|---|
| | 195 | | | | | 200 | | | | | 205 | | | | |

| Thr | Leu | Gly | Thr | Ala | Arg | Met | Leu | Lys | Tyr | Ser | Thr | Gly | Ile | Gly | Ala |
|---|---|---|---|---|---|---|---|---|---|---|---|---|---|---|---|
| 210 | | | | | 215 | | | | | 220 | | | | | |

| Tyr | Ile | Arg | Lys | Phe | Ala | Asn | Gln | His | Asp | Pro | Tyr | Ile | Gly | Tyr | Tyr |
|---|---|---|---|---|---|---|---|---|---|---|---|---|---|---|---|
| 225 | | | | | 230 | | | | | 235 | | | | | 240 |

| Ile | Leu | Arg | Lys | Met | Leu | Ile | Ala | Pro | Thr | Leu | Lys | Met | Leu | Leu | Ala |
|---|---|---|---|---|---|---|---|---|---|---|---|---|---|---|---|
| | | | | 245 | | | | | 250 | | | | | 255 | |

| Leu | Leu | Thr | Phe | Asn | Pro | Gly | Lys | Leu | Ala | Tyr | Ser | Phe | Tyr | Asn | Leu |
|---|---|---|---|---|---|---|---|---|---|---|---|---|---|---|---|
| | | | 260 | | | | | 265 | | | | | 270 | | |

| Val | Gly | Ile | Trp | Arg | Gly | Phe | Phe | Ala | Tyr | Gly | Arg |
|---|---|---|---|---|---|---|---|---|---|---|---|
| | 275 | | | | | 280 | | | | | |

<210> SEQ ID NO 15
<211> LENGTH: 1194
<212> TYPE: DNA
<213> ORGANISM: Methylomonas 16a

<400> SEQUENCE: 15

| atggaactgg gtattgtgac gacacatgta ccgccggcca agggctacgg tggcgtctcg | 60 |
|---|---|
| gtgacttgcg gcgtcttgac cagggcgtgg gcggaaatgg gctagagat ggcgctggtt | 120 |
| tcgtcggatg aatccatcga tgggtgcttg aaaccggcgg acgtcaagct gggcgcaagc | 180 |
| gtggatgtcg atttgtaccg ctgttatggc ttcaggcgct gggggttcgg cttgggagcg | 240 |

-continued

```
ataccccagcc tgctgcgcct gtgctggcaa gccccgctcg tgtatatcca tggcgtcgcc    300
acctggccgt cgaccttggc ggcgcttttt tgctgcctgc tgcgcaagcc gttcatggtg    360
gcggtgcatg gcggcctgat gcctgagcat gtggcactga tcaagcggaa aaaacggcat    420
aaatggtggt attacaaact gctgactttt ccgaccttgc gccgcgcgat tgccgtgcat    480
tgcaccagtg ataccgaggt tgagggcgtg cgtgacgtac tgggcgaaaa cgcgcgggtg    540
ttgctggtgc ccaacggcat cgacagccgg ggtgtcgagg aggccccctta tccggcaggc    600
gaaggcatgc aactgtgttt tttgggtcac gtgcagcagg aaaagggcat caacgctttc    660
atccgggcct ggctcgaggt ccggcggccg ggcgatcgtc tggtcgtcgc cggccgtagc    720
gtggacgggg attattttgc cgagttttgt tccctggtcg aacgggcaaa cggcgcgatc    780
cgctattgcg gctatctgca gcgtgacgac gtgatggcct tgctggcgca agtcattttt    840
ctggtattgc cgtccggttt ggagcaggtc ggcggcatgc gggagaattt cggtaacgtg    900
gtggcggaag ccctggcggc gggacggccg gtgctggttg tcagggggctt ggcctgggat    960
catttgccgg cattgaatgc gggcttggtt tttgacaggg acgaggccgc cgtccaagcc   1020
gtgctacgcc gggctcaggc gctcgatcaa gccgactggc tgcgcatgtc gcaagcgggc   1080
cggcgccatg ttcaacagca gctcgatccg gtcaaactgg cggagcgcgt ctggcaagca   1140
atgacggcgc cggtaccggt tgacgaggcc aaggtgttgg ccgaggagcc gaaa         1194
```

<210> SEQ ID NO 16
<211> LENGTH: 398
<212> TYPE: PRT
<213> ORGANISM: Methylomonas 16a

<400> SEQUENCE: 16

```
Met Glu Leu Gly Ile Val Thr Thr His Val Pro Pro Ala Lys Gly Tyr
  1               5                  10                  15

Gly Gly Val Ser Val Thr Cys Gly Val Leu Thr Arg Ala Trp Ala Glu
             20                  25                  30

Met Gly Leu Glu Met ala Leu Val Ser Ser Asp Glu Ser Ile Asp Gly
         35                  40                  45

Cys Leu Lys Pro Ala Asp Val Lys Leu Gly Ala Ser Val Asp Val Asp
     50                  55                  60

Leu Tyr Arg Cys Tyr Gly Phe Arg Arg Trp Gly Phe Gly Leu Gly Ala
 65                  70                  75                  80

Ile Pro Ser Leu Leu Arg Leu Cys Trp Gln Ala Pro Leu Val Tyr Ile
                 85                  90                  95

His Gly Val Ala Thr Trp Pro Ser Thr Leu Ala Ala Leu Phe Cys Cys
            100                 105                 110

Leu Leu Arg Lys Pro Phe Met Val Ala Val His Gly Gly Leu Met Pro
        115                 120                 125

Glu His Val Ala Leu Ile Lys Arg Lys Lys Arg His Lys Trp Trp Tyr
    130                 135                 140

Tyr Lys Leu Leu Thr Phe Pro Thr Leu Arg Arg Ala Ile Ala Val His
145                 150                 155                 160

Cys Thr Ser Asp Thr Glu Val Glu Gly Val Arg Asp Val Leu Gly Glu
                165                 170                 175

Asn Ala Arg Val Leu Leu Val Pro Asn Gly Ile Asp Ser Arg Gly Val
            180                 185                 190

Glu Glu Ala Pro Tyr Pro Ala Gly Glu Gly Met Gln Leu Cys Phe Leu
        195                 200                 205
```

```
Gly His Val Gln Gln Glu Lys Gly Ile Asn Ala Phe Ile Arg Ala Trp
            210                 215                 220

Leu Glu Val Arg Arg Pro Gly Asp Arg Leu Val Val Ala Gly Arg Ser
225                 230                 235                 240

Val Asp Gly Asp Tyr Phe Ala Glu Phe Cys Ser Leu Val Glu Arg Ala
                    245                 250                 255

Asn Gly Ala Ile Arg Tyr Cys Gly Tyr Leu Gln Arg Asp Asp Val Met
                260                 265                 270

Ala Leu Leu Ala Gln Ser His Phe Leu Val Leu Pro Ser Gly Leu Glu
            275                 280                 285

Gln Val Gly Gly Met Arg Glu Asn Phe Gly Asn Val Val Ala Glu Ala
            290                 295                 300

Leu Ala Ala Gly Arg Pro Val Leu Val Val Arg Gly Leu Ala Trp Asp
305                 310                 315                 320

His Leu Pro Ala Leu Asn Ala Gly Leu Val Phe Asp Arg Asp Glu Ala
                325                 330                 335

Ala Val Gln Ala Val Leu Arg Arg Ala Gln Ala Leu Asp Gln Ala Asp
                340                 345                 350

Trp Leu Arg Met Ser Gln Ala Gly Arg Arg His Val Gln Gln Gln Leu
            355                 360                 365

Asp Pro Val Lys Leu Ala Glu Arg Val Trp Gln Ala Met Thr Ala Ala
            370                 375                 380

Val Pro Val Asp Glu Ala Lys Val Leu Ala Glu Glu Pro Lys
385                 390                 395

<210> SEQ ID NO 17
<211> LENGTH: 951
<212> TYPE: DNA
<213> ORGANISM: Methylomonas 16a

<400> SEQUENCE: 17
atgacgcata aggttggact cgtcgtaccc accttgaatg cgggcgcatc ctggcagggc      60
tggctggagg ccctggcggc gcaaagtcga aggccggatc gtttgttgct gatcgattcc     120
tcgtccagcg acgacacggt ggcgctggcc cgtgcgagag atttgacgc gcatgtgatt      180 gccaaggcct cgttcaacca cggcggcact cgtcaatcgg cgtcgatat gttggtcgac      240 atggatctga tcgtatttct gacccaggat gccttgttgg ccgaccccag cgcgatcgaa     300
aatctgttgc aggtatttgt caatccgcaa gtggccgcgg cctatggccg gcaattgccg     360
catcggaacg ctggccccat cggcgcgcat gcccggatat caattacccc ggcgcaaagc     420
cagttgcgca ccttgcagga ccgcgaccgc ttcggcatca agaccgtgtt catttccaat     480
tcgttcgccg cctacagacg ttgcgccctg atgcaaatcg gcggattccc ggctcacacc     540
attatgaacg aagatactta cgttgccggc aagatgctgt tgtccggctg gagcctcgcc     600
tattgcgccg acgcgcgggt gtttcattcc cacgattaca gcctgctgga agaattcagg     660
cgctatttcg atatcggggt tttccacgcg caaaaccccct ggctgcaaca gacctttggc     720
ggcgcctcgg gcgaaggcgc gcgttttgtg ctctccgaaa tgcgttactt gtcgaacacg     780
gcgccctggc tgatgttttc gcgttcctg agaacgggat tgaaatgggc ggggtataag     840
ctgggcggcc tgcatcgcgg ctggccatta gccctgagca ggcgcctcag cctgcataag     900
ggatattggg tggcaactga acgggaatac cctaatatgc ctggatgccg t              951

<210> SEQ ID NO 18
<211> LENGTH: 317
```

```
<212> TYPE: PRT
<213> ORGANISM: Methylomonas 16a

<400> SEQUENCE: 18

Met Thr His Lys Val Gly Leu Val Val Pro Thr Leu Asn Ala Gly Ala
 1               5                  10                  15

Ser Trp Gln Gly Trp Leu Glu Ala Leu Ala Ala Gln Ser Arg Arg Pro
            20                  25                  30

Asp Arg Leu Leu Leu Ile Asp Ser Ser Ser Ser Asp Asp Thr Val Ala
        35                  40                  45

Leu Ala Arg Ala Arg Gly Phe Asp Ala His Val Ile Ala Lys Ala Ser
    50                  55                  60

Phe Asn His Gly Gly Thr Arg Gln Ser Gly Val Asp Met Leu Val Asp
65                  70                  75                  80

Met Asp Leu Ile Val Phe Leu Thr Gln Asp Ala Leu Leu Ala Asp Pro
                85                  90                  95

Ser Ala Ile Glu Asn Leu Leu Gln Val Phe Val Asn Pro Gln Val Ala
            100                 105                 110

Ala Ala Tyr Gly Arg Gln Leu Pro His Arg Asn Ala Gly Pro Ile Gly
        115                 120                 125

Ala His Ala Arg Ile Phe Asn Tyr Pro Ala Gln Ser Gln Leu Arg Thr
    130                 135                 140

Leu Gln Asp Arg Asp Arg Phe Gly Ile Lys Thr Val Phe Ile Ser Asn
145                 150                 155                 160

Ser Phe Ala Ala Tyr Arg Arg Cys Ala Leu Met Gln Ile Gly Gly Phe
                165                 170                 175

Pro Ala His Thr Ile Met Asn Glu Asp Thr Tyr Val Ala Gly Lys Met
            180                 185                 190

Leu Leu Ser Gly Trp Ser Leu Ala Tyr Cys Ala Asp Ala Arg Val Phe
        195                 200                 205

His Ser His Asp Tyr Ser Leu Leu Glu Glu Phe Arg Arg Tyr Phe Asp
    210                 215                 220

Ile Gly Val Phe His Ala Gln Asn Pro Trp Leu Gln Gln Thr Phe Gly
225                 230                 235                 240

Gly Ala Ser Gly Glu Gly Ala Arg Phe Val Leu Ser Glu Met Arg Tyr
                245                 250                 255

Leu Ser Asn Thr Ala Pro Trp Leu Met Phe Ser Ala Phe Leu Arg Thr
            260                 265                 270

Gly Leu Lys Trp Ala Gly Tyr Lys Leu Gly Gly Leu His Arg Gly Trp
        275                 280                 285

Pro Leu Ala Leu Ser Arg Arg Leu Ser Leu His Lys Gly Tyr Trp Val
    290                 295                 300

Ala Thr Glu Arg Glu Tyr Pro Asn Met Pro Gly Cys Arg
305                 310                 315
```

GENES ENCODING EXOPOLYSACCHARIDE PRODUCTION

This application claims the benefit of U.S. Provisional Application Ser. No. 60/229,944, filed Sep. 1, 2000.

FIELD OF THE INVENTION

This invention relates to the field of microbial production of polysaccharides. More specifically, the invention pertains to nucleic acid molecules encoding enzymes involved in biosynthesis of exopolysaccharides from Methylomonas sp.

BACKGROUND OF THE INVENTION

Polysaccharides are sugar polymers that have been used widely as a thickener in food and non-food industries (Sanford et al. *Pure & Appl. Chem.* 56: 879–892 (1984); Sutherland, *Trends Biotechnol,* 16(1): 41–6 (1998)). They can be found in food products such as salad dressing, jam, frozen food, bakery products, canned food and dry food. Many other applications include suspending agents for pesticides, paints and other coating agents. They can act as flocculants, binders, film-formers, lubricants and friction reducers. Furthermore, exopolysaccharides are commonly used in oil field for oil recovery.

Traditionally, industrially useful polysaccharides have been derived from algal and plant sources. Over the past decade polysaccharides derived from microbes have been found increased usage (Sanford et al. *Pure & Appl. Chem.* 56: 879–892 (1984)); Sutherland, *Trends Biotechnol,* 16(1): 41–6 (1998)). One of the commercially well-known microbial exopolysaccharide is xanthan gum. Xanthan gum is a complex exopolysaccharide produced by a gram-negative bacterium *Xanthomonas campestris* pv. *Campestris* which is a pathogen of cruciferous plants. Xanthan consists of a β-1,4-linked D-glucose backbone with trisaccharides side chains composed of mannose-(β-1,4)-glucuronic acid-(β-1,2)-mannose attached to alternate glucose residues in the backbone by α-1,3 linkages. The polymerized pentasaccharide repeating units which are assembled by the sequential addition of glucose 1-phosphate, glucose, mannose, glucuronic acid, and mannose on polyprenol phosphate carrier (Ielpi et al., *J. Bacteriol.* 175:2490–2500, 1993).

One of the most characterized pathways for the production of microbial exopolysaccharides is found in Xanthomonas. For example, the biosynthetic pathway of xanthan in *Xanthomonas campestris* comprises five stages: (i) conversion of simple sugars to nucleotidyl derivative precursors, (ii) assembly of pentasaccharide subunits attached to the inner membrane polyprenol phosphate carrier, (iii) addition of acetyl and pyruvate groups, (iv) polymerization of pentasaccharide repeat units, and (v) secretion of polymer.

Several enzymes or proteins involved in biosynthesis of xanthan and other exopolysaccharides are well known in the art. UDP-glucose pyrophosphorylase is the enzyme that catalyzes the reaction generating UDP-glucose (UTP+glucose-1-phosphate <--> UDP-glucose+Ppi) (Wei et al., *Biochem Biophys Res Commun.* 226:607–12 (1996)). UDP-glucose is the building blocks for many exopolysaccharides containing glucose.

A cluster of gum genes are found to be required for xanthan gum synthesis in *Xanthomonas campestris* (Katzen et al. *J. Bacteriol.* 180:1607–1617 (1998); Chou, F. L., et al, *Biochem. Biophys. Res. Commun.* 233 (1), 265–269 (1997)). For example, GumD, the glycosyltransferase, is responsible for the transfer of the first glucose to the lipid-linked intermediates in exopolysaccharide biosynthesis in *Xanthomonas campestris*. GumH is the protein involved in the transfer of the mannose to the lipid-linked intermediates in exopolysaccharide synthesis in *Xanthomonas campestris*.

Many other genes involved in exopolysaccharide biosynthesis have been characterized or sequenced from other organisms. The epsB gene encodes the EpsB protein that is probably involved in polymerization and/or export of EPS, has been sequenced in *Ralstonia sola* (Huang et al, *Mol. Microbiol.* 16: 977–989 (1995). The espM gene encoding EspM protein has been found in the esp gene cluster from *Streptococcus thermophilus* (Stingele et al, *J. Bacteriol.* 178: 1680–1690 (1996)). Another putative polysaccharide export protein, WZA, is identified in *E. coli*. (Blattner et al., *Science* 277: 1453–1474 (1997)). Finally, the epsV gene encodes the EpsV protein, a transferase which transfers the sugar to polysaccharide intermediates, and it has also been sequence in *Streptococcus thermophilus* (Bourgoin et al. *Plasmid* 40: 44–49 (1998); Bourgoin,F., et al., *Gene* 233:151–161 (1999).

In spite of the abundance of information regarding gene encoding microbial exopolysaccharides, no genes involved in this pathway have been isolated or characterized from C1 utilizing organisms, such as Methylomonas. As noted above, microbial exopolysaccharides have a variety of uses and it would be an advantage to synthesize this material from an abundance and inexpensive carbon source such as methane.

The problem to be solved therefore is to identify the genes relevant to exopolysaccharide synthesis in a C1 utilizing organism for the production of exopolysaccharides in both similar and unrelated microbes. Applicants have solved the stated problem by isolating and characterizing a complete enzymatic pathway for the synthesis of exopolysaccharide from a *Methylomonas sp*.

SUMMARY OF THE INVENTION

The present invention provides an isolated nucleic acid molecule encoding a *Methylomonas sp* exopolysaccharide biosynthetic enzyme, selected from the group consisting of: (a) an isolated nucleic acid molecule encoding the amino acid sequence selected from the group consisting of SEQ ID NOs:2, 4, 6, 8, 10, 12, 14, 16, and 18; (b) an isolated nucleic acid molecule that hybridizes with (a) under the following hybridization conditions: 0.1×SSC, 0.1% SDS, 65° C. and washed with 2×SSC, 0.1% SDS followed by 0.1×SSC, 0.1% SDS; and (c) an isolated nucleic acid molecule that is complementary to (a) or (b).

Specifically the invention provides: 1) an isolated nucleic acid molecule comprising a first nucleotide sequence encoding a polypeptide of at least 293 amino acids that has at least 58% identity based on the Smith-Waterman method of alignment when compared to a polypeptide having the sequence as set forth in SEQ ID NO:2, or a second nucleotide sequence comprising the complement of the first nucleotide sequence; 2) an isolated nucleic acid molecule comprising a first nucleotide sequence encoding a polypeptide of at least 473 amino acids that has at least 36% identity based on the Smith-Waterman method of alignment when compared to a polypeptide having the sequence as set forth in SEQ ID NO:4, or a second nucleotide sequence comprising the complement of the first nucleotide sequence; 3) an isolated nucleic acid molecule comprising a first nucleotide sequence encoding a polypeptide of at least 366 amino acids that has at least 36% identity based on the Smith-Waterman method of alignment when compared to a polypeptide having the sequence as set forth in SEQ ID NO:6, or a second nucleotide sequence comprising the complement of the first nucleotide sequence; 4) an isolated nucleic acid molecule comprising a first nucleotide sequence encoding a polypeptide of at least 779 amino acids that has at least 35% identity based on the Smith-Waterman method of alignment when compared to a polypeptide having the sequence as set forth in SEQ ID NO:8, or a second nucleotide sequence comprising the complement of the first nucleotide sequence; 5) an isolated nucleic acid molecule comprising a first nucleotide sequence encoding a polypeptide of at least 472 amino acids that has at least 23% identity based on the Smith-Waterman method of alignment when compared to a polypeptide having the sequence as set forth in SEQ ID NO:10, or a second nucleotide sequence comprising the complement of the first nucleotide sequence; 6) an isolated nucleic acid molecule comprising a first nucleotide sequence encoding a polypeptide of at least 272 amino acids that has at least 28% identity based on the Smith-Waterman method of alignment when compared to a polypeptide having the sequence as set forth in SEQ ID NO:12, or a second nucleotide sequence comprising the complement of the first nucleotide sequence; 7) an isolated nucleic acid molecule comprising a first nucleotide sequence encoding a polypeptide of at least 284 amino acids that has at least 21% identity based on the Smith-Waterman method of alignment when compared to a polypeptide having the sequence as set forth in SEQ ID NO:14, or a second nucleotide sequence comprising the complement of the first nucleotide sequence; 8) an isolated nucleic acid molecule comprising a first nucleotide sequence encoding a polypeptide of at least 398 amino acids that has at least 26% identity based on the Smith-Waterman method of alignment when compared to a polypeptide having the sequence as set forth in SEQ ID NO:16, or a second nucleotide sequence comprising the complement of the first nucleotide sequence, and 9) an isolated nucleic acid molecule comprising a first nucleotide sequence encoding a polypeptide of at least 317 amino acids that has at least 51% identity based on the Smith-Waterman method of alignment when compared to a polypeptide having the sequence as set forth in SEQ ID NO:18, or a second nucleotide sequence comprising the complement of the first nucleotide sequence.

The invention also provides chimeric genes comprising the isolated nucleic acid molecule of any one of the instant sequences operably linked to suitable regulatory sequences. The invention additionally provides polypeptides encoded by the instant genes.

Similarly the invention provides a transformed host cell comprising the instant chimeric genes.

Additionally the invention provides a method of obtaining a nucleic acid molecule encoding a Methylomonas sp exopolysaccharide biosynthetic enzyme comprising: (a) probing a genomic library with the nucleic acid molecule of the present invention; (b) identifying a DNA clone that hybridizes with the nucleic acid molecule of the present invention; and (c) sequencing the genomic fragment that comprises the clone identified in step (b), wherein the sequenced genomic fragment encodes a Methylomonas sp exopolysaccharide biosynthetic enzyme.

Alternatively the invention provides a method of obtaining a nucleic acid molecule encoding a Methylomonas sp exopolysaccharide biosynthetic enzyme comprising: (a) synthesizing at least one oligonucleotide primer corresponding to a portion of the sequence selected from the group consisting of SEQ ID NOs:1, 3, 5, 7, 9, 11, 13, 15, and 17; and (b) amplifying an insert present in a cloning vector using the oligonucleotide primer of step (a); wherein the amplified insert encodes a portion of an amino acid sequence encoding a Methylomonas sp exopolysaccharide biosynthetic enzyme.

In one embodiment the invention provides a method for the production of exopolysaccharide comprising: contacting a transformed host cell under suitable growth conditions with an effective amount of a carbon source whereby exopolysaccharide is produced, said transformed host cell comprising a set of nucleic acid molecules encoding SEQ ID NOs:2, 4, 6, 8, 10, 12, 14, 16, and 18; under the control of suitable regulatory sequences.

In an alternate embodiment the invention provides a mutated nucleic acid molecule encoding a Methylomonas sp exopolysaccharide biosynthetic enzyme having an altered biological activity produced by a method comprising the steps of:

(i) digesting a mixture of nucleotide sequences of the present invention or 5–13 with restriction endonucleases wherein said mixture comprises:
  a) a native microbial gene;
  b) a first population of nucleotide fragments which will hybridize to said native microbial sequence;
  c) a second population of nucleotide fragments which will not hybridize to said native microbial sequence; wherein a mixture of restriction fragments are produced;

(ii) denaturing said mixture of restriction fragments;

(iii) incubating the denatured said mixture of restriction fragments of step (ii) with a polymerase;

(iv) repeating steps (ii) and (iii) wherein a mutated microbial gene is produced encoding a protein having an altered biological activity.

BRIEF DESCRIPTION OF THE DRAWINGS, SEQUENCE DESCRIPTIONS AND BIOLOGICAL DEPOSITS

FIG. 1 shows the DNA region containing gumD, wza, espB, espM, waaE, espV, gumH and glycosyltransferase genes in *Methylomonas spp.* strain 16a. The gene encoding the gene ugp, UDP-glucose pyrophosphorylase, is located in a different region.

The invention can be more fully understood from the following detailed description and the accompanying sequence descriptions which form a part of this application.

The following sequence descriptions and sequences listings attached hereto comply with the rules governing nucleotide and/or amino acid sequence disclosures in patent applications as set forth in 37 C.F.R. §1.821–1.825. The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37C.F.R. §1.822.

SEQ ID NO:1 is the nucleotide sequence of the ugp gene.

SEQ ID NO:2 is the deduced amino acid sequence of ugp gene encoded by SEQ ID NO:1.

SEQ ID NO:3 is the nucleotide sequence of ORF 1 comprising the gumD gene.

SEQ ID NO:4 is the deduced amino acid sequence of the gumD gene product encoded by ORF 3.

SEQ ID NO:5 is the nucleotide sequence of ORF 2 comprising the wza gene.

SEQ ID NO:6 is the deduced amino acid sequence of wza the gene product encoded by ORF 5.

SEQ ID NO:7 is the nucleotide sequence of ORF 3 comprising the epsB gene.

SEQ ID NO:8 is the deduced amino acid sequence of epsB the gene product encoded by ORF 7.

SEQ ID NO:9 is the nucleotide sequence of ORF 4 comprising the epsM gene.

SEQ ID NO:10 is the deduced amino acid sequence of the epsM gene product encoded by ORF 9.

SEQ ID NO:11 is the nucleotide sequence of ORF 5 comprising the waaE gene.

SEQ ID NO:12 is the deduced amino acid sequence of the waaE gene product encoded by ORF 11.

SEQ ID NO:13 is the nucleotide sequence of ORF 6 comprising the epsV gene.

SEQ ID NO:14 is the deduced amino acid sequence of the epsV gene product encoded by ORF 13.

SEQ ID NO:15 is the nucleotide sequence of ORF 7 comprising the gumH gene.

SEQ ID NO:16 is the deduced amino acid sequence of the gumH gene product encoded by ORF 15.

SEQ ID NO:17 is the nucleotide sequence of ORF 8 comprising the glycosyltransferase gene.

SEQ ID NO:18 is the deduced amino acid sequence of the glycosyltransferase gene product encoded by ORF 17.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| Methylomanas 16a | ATCC PTA 2402 | Aug. 22, 2000 |

DETAILED DESCRIPTION OF THE INVENTION

Nucleic acid fragments involved in encoding enzymes for exopolysaccharide production have been isolated from a strain of *Methylomonas spp.* strain16a and identified by comparison to public databases containing nucleotide and protein sequences using the BLAST and FASTA algorithms well known to those skilled in the art.

The genes described in present invention enable the overexpression of enzymes involved in the biosynthetic pathway of exopolysaccharide. Overexpression of genes in the present invention in either natural host, Methylomonas 16a, or in heterologous hosts will lead to improved exopolysaccharide yield, saving both and money. In addition, the genes of the present invention can be mutagenized or recombined with genes from other pathways to produce enzymes with different substrate specificity, producing new polymers with novel functionality. Such novel functionality may include novel gelling properties, temperature resistance, and suspending ability.

In some circumstances the production of exopolysaccharides is detrimental and a system of screening for inhibitors of exopolysaccharides synthesis will be useful. For example, in nature, exopolysaccharides are believed to play an important in facilitating bacterial adhesion and the formation of biofilms. Bacterial biofilms are implicated in biofouling and clogging of pipelines in manufacturing processes that use bacteria as a production platform. Similarly in medical environments the formation of bacterial biofilms is problematic. For example, once a biofilm is formed on transplants or catheters, infection caused by bacteria is very difficult to eradicate. Therefore, inhibitors of biofilm formation will have very significant commercial value, and the genes or the gene products described here can be used as targets for screening potential inhibitors.

In this disclosure, a number of terms and abbreviations are used. The following definitions are provided.

"Open reading frame" is abbreviated ORF.

"Polymerase chain reaction" is abbreviated PCR.

As used herein, the terms an "isolated nucleic acid fragment" and "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "ugp" refers to a gene encoding UDP-glucose pyrophosphorylase, UGP.

The term "gumD" refers to a gene encoding glycosyltransferase, GumD.

The term "wza" refers to a gene encoding polysaccharide export protein Wza.

The term "epsB" refers to a gene encoding polysaccharide export protein EpsB.

The term "epsM" refers to a gene encoding polysaccharide biosynthesis related protein EpsM.

The term "waaE" refers to a gene encoding glycosyltransferase, WaaE.

The term "epsV" refers to a gene encoding sugar transferase EpsV.

The term "gumH" refers to a gene encoding galactosyltransferase, GumH.

The term "UDP" refers to uridine 5-diphosphate.

The term "UTP" refers to uridine 5-triphosphate.

As used herein the term "exopolysaccharide" or "polysaccharide" "biosynthetic pathway" means an enzymatic pathway comprising genes ugp, gumD, wza, epsB, epsM, waaE, epsV, and gumH as described above. The term "exopolysaccharide gene" or "polysaccharide gene" will refer to anyone or all of the genes ugp, gumD, wza, epsB, epsM, waaE, epsV, and gumH. The term "exopolysaccharide biosynthetic enzyme" or "polysaccharide biosynthetic enzyme" will refer to anyone or all of the gene products of the genes ugp, gumD, wza, epsB, epsM, waaE, epsV, and gumH.

The term "monosaccharide" will refer to single polyhydroxy aldehyde or ketone units of the general formula $(CH_2O)n$. "Polysaccharides" are molecules containing many monosaccharide units joined in long linear or branched chains. The term "exopolysaccharide" will mean any biologically produced polysaccharide that is excreted from a cell.

The term "Embden-Meyerhof pathway" refers to the series of biochemical reactions for conversion of hexoses such as glucose and fructose to important cellular 3 carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerhof pathway are the phosphofructokinase and fructose 1,6 bisphosphate aldolase.

The term "Entner-Douderoff pathway" refers to a series of biochemical reactions for conversion of hexoses such as as glucose or fructose to important 3 carbon cellular intermediates pyruvate and glyceraldehyde 3 phosphate without any net production of biochemically useful energy. The key enzymes unique to the Entner-Douderoff pathway are the 6 phosphogluconate dehydratase and the ketodeoxyphosphogluconate aldolase.

The term "high growth methanotrophic bacterial strain" refers to a bacterium capable of growth with methane or methanol as sole carbon and energy source which possess a functional Embden-Meyerhof carbon flux pathway resulting in yield of cell mass per gram of C1 substrate metabolized. The specific "high growth methanotrophic bacterial strain" described herein is referred to as "Methylomonas 16a" or "16a", which terms are used interchangeably.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript. It is therefore understood that the invention encompasses more than the specific exemplary sequences.

For example, it is well known in the art that alterations in a gene which result in the production of a chemically equivalent amino acid at a given site, but do not effect the functional properties of the encoded protein are common. For the purposes of the present invention substitutions are defined as exchanges within one of the following five groups:

1. Small aliphatic, nonpolar or slightly polar residues: Ala, Ser, Thr (Pro, Gly);
2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product.

In many cases, nucleotide changes which result in alteration of the N-terminal and C-terminal portions of the protein molecule would also not be expected to alter the activity of the protein.

Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1× SSC, 0.1% SDS, 65° C. and washed with 2×SSC, 0.1% SDS followed by 0.1×SSC, 0.1% SDS), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the DNA sequence of the nucleic acid fragments reported herein. Most preferred are nucleic acid fragments that are at least 95% identical to the DNA sequence of the nucleic acid fragments reported herein.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:2, 4, 6, 8, 10, 12, 14, 16, and 18. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to an RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

The term "signal peptide" refers to an amino terminal polypeptide preceding the secreted mature protein. The signal peptide is cleaved from and is therefore not present in the mature protein. Signal peptides have the function of directing and translocating secreted proteins across cell membranes. Signal peptide is also referred to as signal protein.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual,* Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions,* Cold Spring Harbor Laboratory Cold Press Spring Harbor, N.Y. (1984); and by Ausubel, F. M. et al., *Current Protocols in Molecular Biology,* published by Greene Publishing Assoc. and Wiley-lnterscience (1987).

Isolation of Homologs

The nucleic acid fragments of the instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor, S. et al., *Proc. Acad. Sci.* USA 82, 1074, (1985)) or strand displacement amplification (SDA, Walker, et al., *Proc. Natl. Acad. Sci. U.S.A.,* 89, 392, (1992)).

For example, genes encoding similar proteins or polypetides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach,* K. E. Davis Ed., (1986) pp. 33–50 IRL Press, Herndon, Va.); Rychlik, W. (1993) In White, B. A. (ed.), *Methods in Molecular Biology,* Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991)*Nucl. Acids Res.* 19:5143–5151]. Suitable chaotropic agents include guanidinium chloride, guanidinium thiocyanate, sodium thiocyanate, lithium tetrachloroacetate sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCL, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL., fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitableis the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Recombinant Expression—Microbial

The genes and gene products of the instant sequences may be produced in heterologous host cells, particularly in the cells of microbial hosts. Expression in recombinant microbial hosts may be useful for the expression of various pathway intermediates; for the modulation of pathways already existing in the host for the synthesis of new products heretofore not possible using the host. Additionally the gene products may be useful for conferring higher growth yields of the host or for enabling alternative growth mode to be utilized.

Preferred heterologous host cells for express of the instant genes and nucleic acid molecules are microbial hosts that can be found broadly within the fungal or bacterial families and which grow over a wide range of temperature, pH values, and solvent tolerances. Because of transcription, translation and the protein biosynthetic apparatus is the same irrespective of the cellular feedstock, functional genes are expressed irrespective of carbon feedstock used to generate cellular biomass. Large scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strain s include but are not limited to fungal or yeast species such as Aspergillus, Trichoderma, Saccharomyces, Pichia, Candida, Hansenula, or bacterial species such as Salmonella, Bacillus, Acinetobacter, Rhodococcus, Streptomyces, Escherichia, Pseudomonas, Methylomonas, Methylobacter, Alcaligenes, Synechocystis, Anabaena, Thiobacillus, Methanobacterium and Klebsiella.

Of particular interest in the present invention are high growth obligate methanotrophs having an energetically favorable carbon flux pathway. For example Applicants have discovered a specific strain of methanotroph having several pathway features which make it particularly useful for carbon flux manipulation. This type of strain has served as the host in present application and is known as Methylomonas 16a (ATCC PTA 2402).

The present strain contains several anomalies in the carbon utilization pathway. For example, based on genome sequence data, the strain is shown to contain genes for two pathways of hexose metabolism. The Entner-Douderoff athway which utilizes the keto-deoxy phosphogluconate aldolase enzyme is present in the strain. Is generally well accepted that this is the operative pathway in obligate methanotrophs. Also present, however, is the Embden-Meyerhof pathway which utilizes the Fructose bisphosphate aldolase enzyme. It is well known that this pathway is either not present or not operative in obligate methanotrophs. Energetically, the latter pathway is most favorable and allows greater yield of biologically useful energy and ultimately production of cell mass and other cell mass-dependent products in Methylomonas 16a. The activity of this pathway in the present 16a strain has been confirmed through microarray data and biochemical evidence measuring the reduction of ATP. Although the 16a strain has been shown to possess both the Embden-Meyerhof and the Entner-Douderoff pathway enzymes the data suggests that the Embden-Meyerhof pathway enzymes are more strongly expressed than the Entner-Douderoff pathway enzymes. This result is surprising and counter to existing beliefs on the glycolytic metabolism of methanotrophic bacteria. Applicants have discovered other methanotrophic bacteria having this characteristic, including for example, *Methylomonas clara* and *Methylosinus sporium*. It is likely that this activity has remained undiscovered in methanotrophs due to the lack of activity of the enzyme with ATP, the typical phosphoryl donor for the enzyme in most bacterial systems.

A particularly novel and useful feature of the Embden-Meyerhof pathway in strain 16a is that the key phosphofructokinase step is pyrophosphate dependent instead of ATP dependent. This feature adds to the energy yield of the pathway by using pyrophosphate instead of ATP. Because of it's significance in providing an energetic advantage to the strain this gene in the carbon flux pathway is considered diagnostic for the present strain.

In methanotrophic bacteria methane is converted to biomolecules via a cyclic set of reaction known as the ribulose monophosphate pathway or RuMP cycle. This pathway is comprised of three phases, each phases being a series of enzymatic steps. The first step is "fixation" or incorporation of C-1 (formaldehyde) into a pentose to form a hexose or six carbon sugar. This occurs via a condensation reaction between a 5 carbon sugar (pentose) and formaldehyde and is catalyzed by hexulose monophosphate synthase. The second phase is termed "cleavage" and results in splitting of that hexose into two 3 carbon molecules. One of those three carbon molecules is recycled back through the RuMP pathway and the other 3 carbon fragment is utilized for cell growth. In methanotrophs and methylotrophs the RuMP pathway may occur as one of three variants. However only two of these variants are commonly found. The FBPITA (fructose bisphosphotase/Transaldolase) or the KDPG/TA (keto deoxy phosphogluconateltransaldolase) pathway. (Dijkhuizen L., G. E. Devries. The Physiology and biochemistry of aerobic methanol-utilizing gram negative and gram positive bacteria. In: Methane and Methanol Utilizers 1992, ed Colin Murrell and Howard Dalton Plenum Press NY).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly the genes for the other variant involving the keto deoxy phosphogluconate intermediate were also found clustered together. Available literature teaches that these organisms (obligate methylotrophs and methanotrophs) rely solely on the KDPG pathway and that the FBP-dependent fixation pathway is utilized by facultative methylotrophs (Dijkhuizen et al., supra). Therefore the latter observation is expected whereas the former is not. The finding of the FBP genes in and obligate methane utilizing bacterium is both surprising and suggestive of utility. The FBP pathway is energetically favorable to the host microorganism due to the fact that more energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway a methane-utilizing bacterium may have an advantage over other methane utilizing organisms as production platforms for either single cell protein or for any other product derived from the flow of carbon through the RuMP pathway.

Accordingly the present invention provides a method for the production of exopolysaccharide using an energetically, favoralbe Methylomonas strain which (a) grows on a C1 carbon substrate selected from the group consisting of methane and methanol; and (b) comprises a functional Embden-Meyerhof carbon pathway, said pathway comprising a gene encoding a pyrophosphate dependent phosphofructokinase enzyme.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes.

Additionally, the instant genes will be effective in altering the properties of the host microbe. It is expected, for example, host cells can be transformed with chimeric genes encoding one or more of the instant sequences in order to induce the overexpression of exopolysaccharide, or to manipulate production of exopolysaccharides by changing the biosynthesis pathway of exopolysaccharide in host cell to reduce the exopolysaccharide production in host cells to reduce the biofilm formation.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in Saccharomyces); AOX1 (useful for expression in Pichia); and lac, ara, tet, trp, $IP_L$, $IP_R$, T7, tac, and trc (useful for expression in *Escherichia coli*) as well as the amy, apr, npr promoters and various phage promoters useful for expression in Bacillus.

Termination control regions may also be derived from various genes native to the preferred hosts. Optionally, a termination site may be unnecessary, however, it is most preferred if included.

Pathway Engineering

In a preferred embodiment the present genes may be used in various methanotrophic strains to modulate or regulate the production of exopolysaccharides. These genes and their sequences may be used in a variety of ways to modulate existing polysaccharide pathways. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additionally copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some case the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldener et al. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect nonreplicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

Within the context of the present invention it may be useful to modulate the expression of the exopolysacharaide pathway. As has been noted the present strain has the ability to product polysaccharides in large amounts. This process is governed by a set of genes including the ugp gene, gumD and H genes, the epsB, M, and V genes and the waaD gene. In this pathway it may be of particular importance to up-regulate the espB gene involved in polymerization and/or export of the polysaccharide, or the epsV gene which controls the transfer of sugar to polysaccharide intermediates.

Industrial Scale Production

Where commercial production of exopolysaccharides are desired a variety of culture methodologies may be applied. For example, large scale production may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of exopolysaccharides may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.,* [Int. Symp.], 7th (1993), 415–32. Editor(s): Murrell, J. Collin; Kelly, Don P. Publisher: Intercept, Andover, UK). Similarly, various species of Candida will metabolize alanine or oleic acid (Sulter et al., *Arch. Microbiol* 153:485–489 (1990)). Hence it is contemplated that the source of carbon utilized in the present invention may encompass a wide variety of carbon containing substrates and will only be limited by the choice of organism.

Recombinant Production—Plants

Plants and algae are also known to produce polysaccharides. The nucleic acid fragments of the instant invention may be used to create transgenic plants having the ability to express the microbial protein. Preferred plant hosts will be any variety that will support a high production level of the instant proteins. Suitable green plants will included but are not limited to of soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa,* L), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as Spirulina and Dunalliela. Overexpression of the proteins of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.,* 1:483–498 1982)), and the promoter of the chlorophyll a/b binding protein. These two promoters are known to be light-induced in plant cells (See, for example, *Genetic Engineering of Plants, an Agricultural Perspective,* A. Cashmore, Plenum, New York (1983), pages 29–38; Coruzzi, G. et al., *The Journal of Biological Chemistry,* 258:1399 (1983), and Dunsmuir, P. et al., *Journal of Molecular and Applied Genetics,* 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA blots (Southern, *J. Mol. Biol.* 98, 503, (1975)). Northern analysis of mRNA expression (Kroczek, *J. Chromatogr. Biomed. Appl.,* 618 (1–2) (1993) 133–145), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100:1627–1632 (1992)) added and/or with targeting sequences that are already present removed. While the references cited give examples of each of these, the list is not exhaustive and more targeting signals of utility may be discovered in the future that are useful in the invention.

Protein Engineering

It is contemplated that the present nucleotide may be used to produce gene products having enhanced or altered activity. Various methods are known for mutating a native gene sequence to produce a gene product with altered or enhanced activity including but not limited to error prone PCR (Melnikov et al., *Nucleic Acids Research,* (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605,793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The instant microbial sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al, PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

Gene Expression Profiling

All or portion of the nucleic acid fragments of the instant invention may also be used as probes for gene expression monitoring and gene expression profiling. Many external changes such as changes in growth condition, exposure to chemicals, can cause induction or repression of genes in the cell. The induction or repression of gene can be used for a screening system to determine the best growth condition for production organism, drug discovery with similar mode of action compound, just to mention a few. On the other hand, by amplifying or disrupting genes, one can manipulate the production of the amount of cellular products, biofilm formation as well as the timeline.

For example, all or a portion of the instant nucleic acid fragments may be immobilized on a nylon membrane or a glass slide. A Generation II DNA spotter (Molecular Dynamics) is one of the available technology to array the DNA samples onto the coated glass slides. Other array methods are also available and well known in the art. After the cells were grown in various growth conditions or treated with potential candidates, cellular RNA is purified. Fluorescent or radioactive labeled target cDNA can be made by reverse transcription of mRNA. The target mixture is hybridized to the probes, washed using conditions well known in the art. The amount of the target gene expression is quantified by the intensity of radioactivity or fluorescence label (e.g., confocal laser microscope: Molecular Dynamics). The intensities of radioactivity or fluorescent label at the immobilized probes are measured using the technology well known in the art. The two color fluorescence detection scheme (e.g., Cy3 and Cy5) has the advantage over radioactively labeled targets of allowing rapid and simultaneous differential expression analysis of independent samples. In addition, the use of ratio measurements compensates for probe to probe variation of intensity due to DNA concentration and hybridization efficiency. In the case of fluorescence labeling, the two fluorescent images obtained with the appropriate excitation and emission filters constitute the raw data from differential gene expression ratio values are calculated. The intensity of images are analyzed using the available software (e.g., Array Vision 4.0: Imaging Research Inc.) well known in the art and normalized to compensate for the differential efficiencies of labeling and detection of the label. There are many different ways known in the art to normalize the signals. One of the ways to normalize the signal is by correcting the signal against internal controls. Another way is to run a separate array with labeled genomic driven DNA and compare the signal with mRNA driven signals. This method also allows to measure the transcript abundance. The array data of individual gene is examined and evaluated to determine the induction or repression of the gene under the test condition.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology,* Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. In any case where GCG program parameters were not prompted for, in these or any other GCG program, default values were used.

Multiple alignment of the sequences was performed using the the FASTA program incorporating the Smith-Waterman algorithm (W. R. Pearson, *Comput. Methods Genome Res.,* [Proc. Int. Symp.] (1994), Meeting Date 1992, 111–20. Editor(s): Suhai, Sandor. Publisher: Plenum, New York, N.Y.).

The meaning of abbreviations is as follows: "h" means hour(s), "min" means minute(s), "sec" means second(s), "d" means day(s), "mL" means milliliters, "L" means liters.

Isolation of Strain Methylomonas 16a

The original environmental sample containing the isolate was obtained from pond sediment from the nature preserve in Pennsylvania. The pond sediment was inoculated directly into a defined mineral medium under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto defined minimal medium agar and incubated under 25% methane in air. Methylomonas 16a was selected as the organism to study due to the rapid growth of colonies and large colony size. The genus of the selected organism was confirmed by 16SrRNA analysis. 16SrRNA extracted from the strain was sequenced and compared to known 16SrRNAs from other microorganisms. The data shows 96% similarity to sequences from *Methylomonas sp.* KSP III and *Methylomonas sp.* Strain LW13

Example 1

Preparation of Genomic DNA for Sequencing and Sequence Generation

Genomic DNA was isolated from Methylomonas 16a according to standard protocols.

Genomic DNA and library construction were prepared according to published protocols (Friseur et al., The Minimal Gene Complement of *Mycoplasma genitalium; Science* 270, 1995). A cell pellet was resuspended in a solution containing 100 mM Na-EDTA pH 8.0, 10 mM tris-HCl pH 8.0, 400 mM NaCl, and 50 mM MgCl$_2$.

Genomic DNA preparation. After resuspension, the cells were gently lysed in 10% SDS, and incubated for 30 min at 55° C. After incubation at room temperature, proteinase K was added to 100 $\mu$g/mL and incubated at 37° C. until the suspension was clear. DNA was extracted twice with tris-equilibrated phenol and twice with chloroform. DNA was precipitated in 70% ethanol and resuspended in a solution containing 10 mM tris-HCl and 1 mM Na-EDTA (TE) pH 7.5. The DNA solution was treated with a mix of RNAases, then extracted twice with tris-equilibrated phenol and twice with chloroform. This was followed by precipitation in ethanol and resuspension in TE.

Library construction. 200 to 500 $\mu$g of chromosomal DNA was resuspended in a solution of 300 mM sodium acetate, 10 mM tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease. After size fractionation, a fraction (2.0 kb, or 5.0 kb) was excised, cleaned and a two-step ligation procedure was used to produce a high titer library with greater than 99% single inserts.

Sequencing. A shotgun sequencing strategy approach was adopted for the sequencing of the whole microbial genome (Fleischmann, Robert et al., Whole-Genome Random sequencing and assembly of *Haemophilus influenzae* Rd Science, 269:1995).

Sequence was generated on an ABI Automatic sequencer using dye terminator technology (U.S. Pat. No. 5,366,860; EP 272007) using a combination of vector and insert-specific primers. Sequence editing was performed in either DNAStar (DNA Star Inc.) or the Wisconsin GCG program (Wisconsin Package Version 9.0, Genetics Computer Group (GCG), Madison, Wis.) and the CONSED package (version 7.0). All sequences represent coverage at least two times in both directions.

Example 2

Identification and Characterization of Bacterial ORF's

ORFs encoding ugp, gumD, wza, epsB, epsM, waaE, epsV, gumH, and glycosyltransferase of Methylomonas 16a were initially identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant (nr) GenBank CDS translations, sequences derived from the 3-dimensional structure Brookhaven Protein Data Bank, the SWISS-PROT protein sequence database, EMBL, and DDBJ databases). The sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTP algorithm (Altschul, S. F., et al., *Nucleic Acid Res.* 25:3389–3402) (1997) provided by the NCBI.

All initial comparisons were done using either the BLASTNnr or BLASTPnr algorithm. A refined similarity search was performed using FASTA (version 3.2) with the default parameters settings (BLOSUM 50 scoring matrix, word size ktup=2, gap penalty=–12 for the first residue and –2 for every additional residue in the gap). The results of the FASTA comparison is given in Table 1 which summarize the sequences to which they have the most similarity. Table 1 displays data based on the FASTA algorithm with values reported in expect values. The Expect value estimates the statistical significance of the match, specifying the number of matches, with a given score, that are expected in a search of a database of this size absolutely by chance.

Gene clusters of genes, gumD, wza, epsB, epsM, waaE, epsV, gumH, and glycosyltransferase, are shown in FIG. 1.

TABLE 1

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| | ugp | ugp (*Xanthomonas campestris*) | 1 | 2 | 58% | 82% | 3.2 e-60 | Wei et al., Biochem. Biophys. Res. Commun. 226 (3), 607–612 (1996) |
| ORF 1 | gumD | gumD (*Xanthomonas campestris*) | 3 | 4 | 36% | 69% | 2.5 e-52 | Chou, F. L., et el, Biochem. Biophys. Res. Commun. 233 (1), 265–269 (1997) |
| ORF 2 | wza | wza (*Escherichia coli*) | 5 | 6 | 36% | 69% | 5.8 e-39 | Blattner, F. R. et al., Science 277 (5331), 1453–1474 (1997) |
| ORF 3 | epsB | epsB (*Pseudomonas solanacearum*) | 7 | 8 | 35% | 67% | 2 e-74 | Huang, J. and Schell, M., Mol. Microbiol. 16 (5), 977–989 (1995) |
| ORF 4 | epsM | epsM (*Streptococcus thermophilus*) | 9 | 10 | 23% | 55% | 1.3 e-05 | Stingele, F. et al., J. Bacteriol. 178 (6), 1680–1690 (1996) |
| ORF 5 | waaE | waaE (*Serratia marcescens*) | 11 | 12 | 28% | 55% | 8.6 e-09 | Pique, N et al., . Unpublished Genbank number: AAC44433 |
| ORF 6 | epsV | epsv (*Streptococcus thermophilus*) | 13 | 14 | 21% | 56% | 2.3 e-05 | Bourgoin, F. et al., Plasmid 40 (1), 44–49 (1998) |
| ORF 7 | gumH | gumH (*Rhizobium meliloti*) | 15 | 16 | 26% | 55% | 0.00088 | Becker, A. et al., Mol. Microbiol. 16 (2), 191–203 (1995) |
| ORF 8 | glycosyl transferase | Glycosyltransferase (*Actinobacillus actinimycetemcomitans*) | 17 | 18 | 51% | 80% | 1.7 e-62 | Nakano, Y, Biochem. Biophys. Acta 1442:409–414 (1998) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

What is claimed is:

1. A method for the production of exopolysaccharide comprising: contacting a methanotrophic bacteria under suitable growth conditions with an effective amount of a C1 carbon substrate, selected from the group consisting of methane and methanol, wherein said methanotrophic bacteria comprises:

(a) a heterologous nucleic acid molecule encoding SEQ ID NO: 4, under the control of suitable regulatory sequences; and (b) a functional Embden-Meyerhof carbon pathway, said pathway comprising a gene encoding a pyrophosphate dependent phosphofructokinase enzyme;

wherein exopolysaccharide is produced.

2. A method according to claim 1 wherein said methanotrophic bacteria is selected from the group consisting of Methylomonas, Methylobacter, Methanobacterium and Methylosinus.

3. A method according to claim 2 wherein said methanotrophic bacteria is Methylomonas 16a ATCC PTA 2402.

* * * * *